(12) United States Patent
Pugh et al.

(10) Patent No.: US 10,261,344 B2
(45) Date of Patent: Apr. 16, 2019

(54) METHODS FOR FORMING VARIABLE OPTIC OPHTHALMIC DEVICES INCLUDING SHAPED LIQUID CRYSTAL ELEMENTS

(71) Applicant: Johnson & Johnson Vision Care, Inc., Jacksonville, FL (US)

(72) Inventors: Randall B. Pugh, St. Johns, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/198,387

(22) Filed: Jun. 30, 2016

(65) Prior Publication Data
US 2018/0004012 A1 Jan. 4, 2018

(51) Int. Cl.
| | | |
|---|---|---|
| G02F 1/1337 | (2006.01) | |
| G02C 7/08 | (2006.01) | |
| C09K 19/38 | (2006.01) | |
| G01M 11/02 | (2006.01) | |
| G02C 7/04 | (2006.01) | |
| G02C 7/10 | (2006.01) | |
| G02F 1/1341 | (2006.01) | |
| A61F 2/16 | (2006.01) | |
| G02F 1/29 | (2006.01) | |

(52) U.S. Cl.
CPC ............ G02C 7/083 (2013.01); A61F 2/1627 (2013.01); C09K 19/38 (2013.01); G01M 11/0207 (2013.01); G02C 7/04 (2013.01); G02C 7/108 (2013.01); G02F 1/1341 (2013.01); G02F 1/133788 (2013.01); G02F 1/29 (2013.01); G02C 2202/16 (2013.01); G02F 2001/294 (2013.01)

(58) Field of Classification Search
CPC .................................................. G02F 1/133788
See application file for complete search history.

(56) References Cited

U.S. PATENT DOCUMENTS

| | | | |
|---|---|---|---|
| 2010/0041787 A1* | 2/2010 | Chen | C07D 251/24 523/106 |
| 2012/0212696 A1 | 8/2012 | Trajkovska | |
| 2013/0166025 A1 | 6/2013 | Pugh | |
| 2014/0327883 A1* | 11/2014 | Baranton | A61B 3/0083 351/221 |
| 2015/0077662 A1 | 3/2015 | Pugh | |

(Continued)

FOREIGN PATENT DOCUMENTS

| | | |
|---|---|---|
| JP | 2008070508 | 3/2008 |
| WO | WO2015/155748 A1 | 10/2015 |

*Primary Examiner* — Edmond C Lau

(57) ABSTRACT

This invention discloses methods and apparatus for providing an ophthalmic lens of variable optical power. The variable optic insert may have surfaces within that have differing radii of curvature. The variable optic insert may also comprise polarizing elements. In some examples, an intermediate optic piece may be formed to comprise a UV absorbing dye, allowing differential processing of regions on either side of the intermediate optic piece. In some embodiments, an ophthalmic lens is cast-molded from a silicone hydrogel. The various ophthalmic lens entities may include electroactive liquid crystal layers to electrically control refractive characteristics.

14 Claims, 21 Drawing Sheets

(56) References Cited

U.S. PATENT DOCUMENTS

| | | | |
|---|---|---|---|
| 2015/0077700 A1* | 3/2015 | De Sio | G02C 7/04 351/159.03 |
| 2016/0011075 A1* | 1/2016 | Maluck | G01J 3/28 356/125 |
| 2016/0018672 A1 | 1/2016 | Wang | |

* cited by examiner

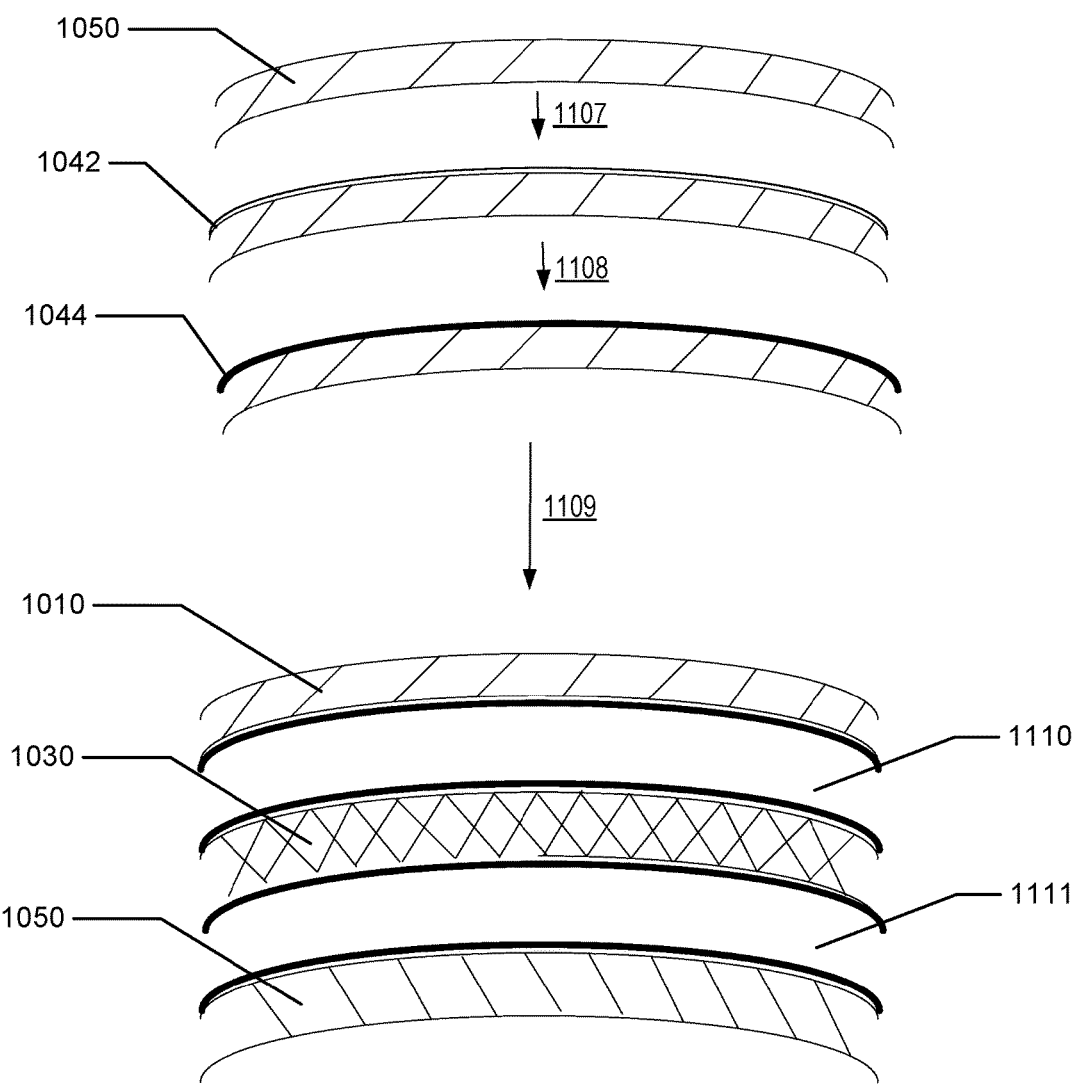

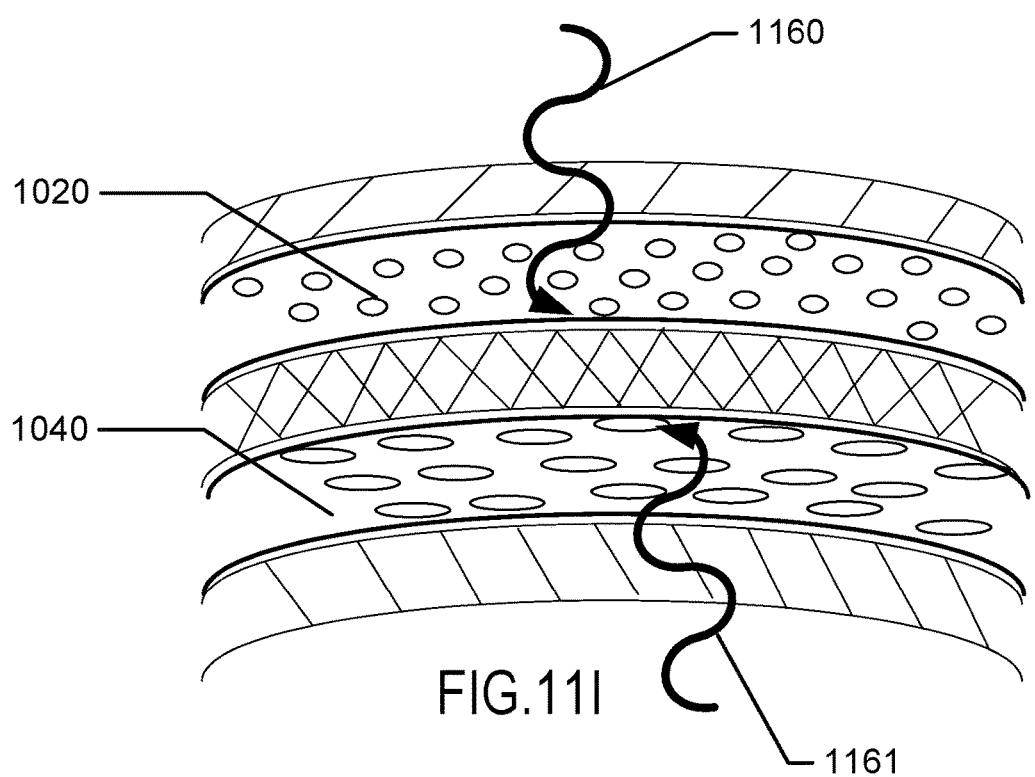

```
┌─────────────────────────────────────────────────────────────────┐
│  FORM FRONT, INTERMEDIATE AND BACK OPTIC PIECES WITH DESIGNED   │
│     OPTICAL CHAMBERS AND ULTRA-VIOLET ABSORBING DYE IN THE      │
│                 INTERMEDIATE CHAMBER              1201          │
└─────────────────────────────────────────────────────────────────┘
                                │
┌─────────────────────────────────────────────────────────────────┐
│ DEPOSIT AN ELECTRODE LAYER UPON THE LOWER SURFACE OF THE FRONT  │
│ OPTIC PIECE, BOTH SURFACES OF THE INTERMEDIATE PIECE AND THE UPPER │
│            SURFACE OF THE BACK OPTIC PIECE        1202          │
└─────────────────────────────────────────────────────────────────┘
                                │
┌─────────────────────────────────────────────────────────────────┐
│    DEPOSIT A PHOTOSENSITIVE ALIGNMENT LAYER UPON THE ELECTRODE  │
│      LAYERS ON THE FRONT, INTERMEDIATE AND BACK OPTIC PIECES    │
│                                                   1203          │
└─────────────────────────────────────────────────────────────────┘
                                │
┌─────────────────────────────────────────────────────────────────┐
│ POSITION THE FRONT OPTIC PIECE ABOVE THE INTERMEDIATE OPTIC PIECE │
│  ABOVE THE BACK OPTIC PIECE ALIGNING THE CHAMBERS TO EACH OTHER │
│          FORMING A STACK WITH A FIRST AND SECOND CAVITY         │
│                                                   1204          │
└─────────────────────────────────────────────────────────────────┘
                                │
┌─────────────────────────────────────────────────────────────────┐
│  IRRADIATE THE FRONT OF THE STACK WITH A FIRST PATTERN OF LIGHT AND │
│     THE BACK OF THE STACK WITH A SECOND PATTERN OF LIGHT AT A   │
│       WAVELENGTH OR A BAND OF WAVELENGTHS THAT INTERACT WITH THE │
│              PHOTO SENSITIVE ALIGNMENT LAYER                    │
│                                                   1205          │
└─────────────────────────────────────────────────────────────────┘
                                │
┌─────────────────────────────────────────────────────────────────┐
│        DEPOSIT LIQUID CRYSTAL INTO THE FIRST AND SECOND CAVITY  │
│                                                   1206          │
└─────────────────────────────────────────────────────────────────┘
                                │
┌─────────────────────────────────────────────────────────────────┐
│         ALLOW THE LIQUID CRYSTAL TO ALIGN WITH THE ALIGNMENT LAYERS │
│                                                   1207          │
└─────────────────────────────────────────────────────────────────┘
                                │
┌─────────────────────────────────────────────────────────────────┐
│         MEASURE THE OPTICAL PERFORMANCE WITH POLARIZED LIGHT THAT │
│   INTERACTS WITH THE LIQUID CRYSTAL ALIGNMENT IN THE FIRST CHAMBER │
│                                                   1208          │
└─────────────────────────────────────────────────────────────────┘
                                │
┌─────────────────────────────────────────────────────────────────┐
│         MEASURE THE OPTICAL PERFORMANCE WITH POLARIZED LIGHT THAT │
│  INTERACTS WITH THE LIQUID CRYSTAL ALIGNMENT IN THE SECOND CHAMBER │
│                                                   1209          │
└─────────────────────────────────────────────────────────────────┘
                                │
┌─────────────────────────────────────────────────────────────────┐
│    ADJUST ONE OR MORE OF THE FIRST, INTERMEDIATE AND/OR BACK    │
│    CHAMBERS TO ADDRESS ANY OPTIMIZATION NEEDS IDENTIFIED BY THE │
│                        MEASUREMENTS               1210          │
└─────────────────────────────────────────────────────────────────┘
                                │
┌─────────────────────────────────────────────────────────────────┐
│           POLYMERIZE THE LIQUD CRYSTAL LAYERS     1211          │
└─────────────────────────────────────────────────────────────────┘
                                │
┌─────────────────────────────────────────────────────────────────┐
│      OPTIONALLY SEAL THE PIECES TOGETHER AT THE EDGES    1212   │
└─────────────────────────────────────────────────────────────────┘
```

FIG. 12

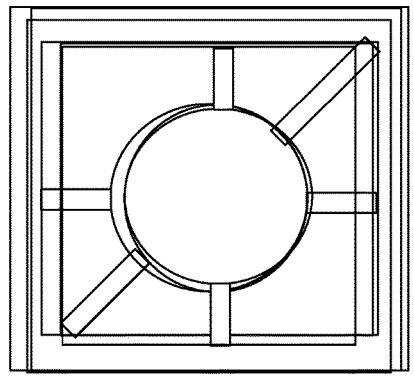
FIG13B
Polarized incident light to wavefront aberrometer
Polarized incident light to wavefront aberrometer
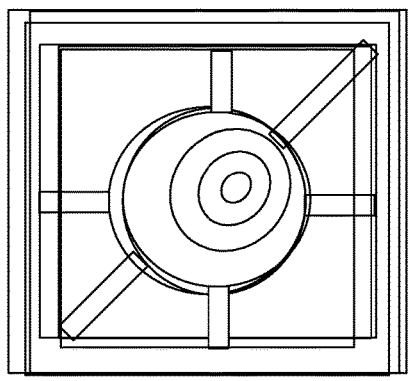
FIG13C
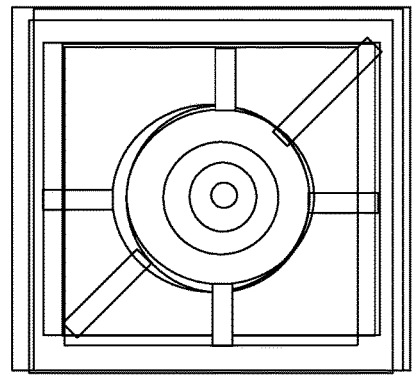
FIG13D

METHODS FOR FORMING VARIABLE OPTIC OPHTHALMIC DEVICES INCLUDING SHAPED LIQUID CRYSTAL ELEMENTS

BACKGROUND OF THE INVENTION

1. Field of the Invention

The present invention relates to an ophthalmic lens device with a variable optic capability and, more specifically, in some embodiments, the fabrication of an ophthalmic lens with a variable optic insert utilizing liquid crystal elements.

2. Discussion of the Related Art

Traditionally an ophthalmic lens, such as a contact lens or an intraocular lens, provided a predetermined optical quality. A contact lens, for example, can provide one or more of vision correcting functionality, cosmetic enhancement, and therapeutic effects, but only a set of vision correction functions. Each function is provided by a physical characteristic of the lens. Basically, a design incorporating a refractive quality into a lens provides vision corrective functionality and this may be utilized for an individual having myopia, hyperopia, astigmatism, myopia and astigmatism, hyperopia with astigmatism, presbyopia and even higher order aberrations. A pigment incorporated into the lens can provide a cosmetic enhancement. An active agent incorporated into a lens can provide a therapeutic functionality.

To date, optical quality in an ophthalmic lens has been designed into the physical characteristic of the lens. Generally, an optical design has been determined and then imparted into the lens during fabrication of the lens, for example, through cast molding, or lathing. The optical qualities of the lens have remained static once the lens has been formed. However, wearers may at times find it beneficial to have more than one focal power available to them in order to provide sight accommodation. Unlike spectacle wearers, who can change spectacles to change an optical correction, contact wearers or those with intraocular lenses have not been able to change the optical characteristics of their vision correction without significant effort or the complementing of spectacles with contact lenses or intraocular lenses.

The methods to fabricate lens inserts and lenses consistent with electroactive liquid crystal lenses may be critical to achieving a commercial product. There may be critical parameters that must be controlled to synthesize a desirable optical result such as control over the polarization angles and centration of lens elements within the optical zone. Therefore, it would be desirable to have improved methods of producing liquid crystal based elements.

SUMMARY OF THE INVENTION

Accordingly, the present invention includes innovations relating to methods of fabricating variable optic inserts with liquid crystal elements that may be energized and incorporated into an ophthalmic device which is capable of changing the optical quality of the lens. Examples of such ophthalmic devices may include a contact lens or an intraocular lens. In addition, methods and apparatus for forming an ophthalmic lens with a variable optic insert with liquid crystal elements are presented. Some embodiments may also include a cast-molded silicone hydrogel contact lens with a rigid or formable energized insert, which additionally includes a variable optic portion, wherein the insert is included within the ophthalmic lens in a biocompatible fashion.

The present invention therefore includes disclosure of an ophthalmic lens with a variable optic insert, an apparatus for forming an ophthalmic lens with a variable optic insert, and methods for manufacturing the same. An energy source may be deposited or assembled onto a variable optic insert and the insert may be placed in proximity to one, or both of, a first mold part and a second mold part. A composition comprising a reactive monomer mixture (hereafter referred to as a reactive monomer mixture) is placed between the first mold part and the second mold part. The first mold part is positioned proximate to the second mold part thereby forming a lens cavity with the energized media insert and at least some of the reactive monomer mixture in the lens cavity. The reactive monomer mixture is then exposed to actinic radiation to form an ophthalmic lens. Lenses are formed via the control of actinic radiation to which the reactive monomer mixture is exposed. In some embodiments, an ophthalmic lens skirt or an insert-encapsulating layer may be comprised of standard hydrogel ophthalmic lens formulations. Exemplary materials with characteristics that may provide an acceptable match to numerous insert materials may include, for example, the Narafilcon family (including Narafilcon A and Narafilcon B), the Etafilcon family (including Etafilcon A), Galyfilcon A and Senofilcon A.

The methods of forming the variable optic insert with liquid crystal elements and the resulting inserts are important aspects of various embodiments. In some embodiments, the liquid crystal may be located between two alignment layers, which may set the resting orientation for the liquid crystal. Those two alignment layers may be in electrical communication with an energy source through electrodes deposited on substrate layers that contain the variable optic portion. The electrodes may be energized through an intermediate interconnect to an energy source or directly through components embedded in the insert.

The energization of the alignment layers may cause a shift in the liquid crystal from a resting orientation to an energized orientation. In embodiments that operate with two levels of energization, on or off, the liquid crystal may only have one energized orientation. In other alternative embodiments, where energization occurs along a scale of energy levels, the liquid crystal may have multiple energized orientations. Still further embodiments may derive where the energization process may cause a switch between different states through an energization pulse.

The resulting alignment and orientation of the molecules may affect light that passes through the liquid crystal layer thereby causing the variation in the variable optic insert. For example, the alignment and orientation may act with refractive characteristics upon the incident light. Additionally, the effect may include alteration of polarization of the light. Some embodiments may include a variable optic insert wherein energization alters a focal characteristic of the lens.

In some embodiments, the liquid crystal layer may be formed in a manner wherein a polymerizable mixture comprising liquid crystal molecules is caused to polymerize. By controlling the polymerization in various manners, droplets of liquid crystal molecules may separate from the polymerized layer as it forms. In some embodiments, the process may be controlled such that the droplets are nano-scaled which may mean that the average or median diameter of the collection of droplets is less than roughly 1 micron in length. In some further versions the average or median diameter may also be less than roughly 0.1 micron in length.

In some embodiments the insert of the ophthalmic device may comprise electrodes made of various materials, including transparent materials such as ITO as a non-limiting example. A first electrode may be located proximate to a back surface of a front curve piece, and a second electrode may be located proximate to a front surface of a back curve piece. When an electric potential is applied across the first and second electrodes, an electric field may be established across a liquid crystal layer located between the electrodes. The application of an electric field across the liquid crystal layer may cause liquid crystal molecules within the layer to physically align with the electric field.

In some embodiments, the ophthalmic devices as described may include a processor.

In some embodiments, the ophthalmic devices as described may include an electrical circuit. The electrical circuit may control or direct electric current to flow within the ophthalmic device. The electrical circuit may control electrical current to flow from an energy source to the first and second electrode elements.

One general aspect includes a method of forming a variable optic insert for an ophthalmic lens device including: forming a front optic piece; forming an intermediate optic piece, where the intermediate optic piece includes a UV absorbing dye; forming a back optic piece; adding a photosensitive alignment layer to surfaces of the front optic piece, the intermediate optic piece, and the back optic piece; placing the intermediate optic piece upon the back optic piece; placing the front optic piece upon the intermediate optic piece, where a combination of the front optic piece, the intermediate optic piece and the back optic piece form a stack; exposing the photosensitive alignment layers underneath the intermediate optic piece with a first polarized irradiation source in a first polarization pattern, where a wavelength of the irradiation is absorbed at least in part by the UV absorbing dye; and exposing the photosensitive alignment layers above the intermediate optic piece with a second polarized irradiation source in a second polarization pattern, where a wavelength of the irradiation is absorbed at least in part by the UV absorbing dye.

Implementations may include one or more of the following features. The method as stated above may further include polymerizing the solution including liquid crystal molecules in the first cavity, and polymerizing the solution including liquid crystal molecules in the second cavity. The method may include examples where the UV absorbing dye includes a benzotriazole-type UV blocker.

One general aspect includes a method of forming a variable optic insert for an ophthalmic lens device including: forming a front optic piece; forming an intermediate optic piece, where the intermediate optic piece includes a UV absorbing dye; forming a back optic piece; adding a photosensitive alignment layer to surfaces of the front optic piece, the intermediate optic piece, and the back optic piece; placing the intermediate optic piece upon the back optic piece; placing the front optic piece upon the intermediate optic piece, where a combination of the front optic piece, the intermediate optic piece and the back optic piece form a stack; exposing the photosensitive alignment layers underneath the intermediate optic piece with a first polarization pattern; exposing the photosensitive alignment layers above the intermediate optic piece with a second polarization pattern; filling a first chamber between the front optic piece with a liquid crystal containing monomer mixture; filing a second chamber between the intermediate optic piece and the back optic piece with a liquid crystal containing monomer mixture; measuring optical characteristics of the stack with a first polarized incident light source; measuring optical characteristics of the stack with a second polarized incident light source: adjusting an orientation of one or both of the front optic piece and the back optic piece; polymerizing the liquid crystal containing monomer mixture in the first chamber; and polymerizing the liquid crystal containing monomer mixture in the second chamber. Methods with a subset of these steps may be possible.

One general aspect includes a method for forming a multi-cavity insert for an ophthalmic device, the method including: forming a front optic piece; forming a back optic piece; forming an intermediate optic piece, where a composition of the intermediate optic piece blocks more than 90% of UV light in a first band of UV light; stacking the front optic piece upon the intermediate optic piece upon the back optic piece, where a first cavity is formed between the front optic piece and the intermediate optic piece and a second cavity is formed between the intermediate optic piece and the back optic piece; irradiating an extent of the first cavity with a source of UV light from a first direction which traverses the front optic piece, where the source of UV light emits light within the first band of UV light, and where the irradiation is incident upon materials within the first cavity; and irradiating an extent of the second cavity with a source of UV light from a second direction which traverses the back optic piece, where the source of UV light emits light within the first band of UV light, and where the irradiation is incident upon materials within the second cavity.

One general aspect includes a contact lens including: an insert including: a first optic piece; a second optic piece; an intermediate optic piece, where the intermediate optic piece includes a UV blocker; an energy source; at least a first and second layer of polymerized material including liquid crystal molecules; and an electronic circuit. The contact lens also includes a hydrogel skirt which encapsulates the insert.

In some embodiments the insert of the ophthalmic device with a front insert piece, a back insert piece and at least a first intermediate insert piece may comprise electrodes made of various materials, including transparent materials such as ITO as a non-limiting example. A first electrode may be located proximate to a back surface of a front curve piece, and a second electrode may be located proximate to a front surface of an intermediate optic piece. When an electric potential is applied across the first and second electrodes, an electric field may be established across a liquid crystal layer located between the electrodes. The application of an electric field across the liquid crystal layer may cause liquid crystal molecules within the layer to physically align with the electric field. In some embodiments, the liquid crystal molecules may be located in droplets within the layer and in some embodiments the droplets may have average diameters less than 1 micron in dimension. When the liquid crystal molecules align with the electric filed, the alignment may cause a change in the optical characteristics that a light ray may perceive as it traverses the layer containing liquid crystal molecules. A non-limiting example may be that the index of refraction may be altered by the change in alignment. In some embodiments, the change in optical characteristics may result in a change in focal characteristics of the lens which contains the layer containing liquid crystal molecules.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 11A-11I illustrate exemplary method steps in fabricating electroactive liquid crystal based lens elements.

FIG. 12 illustrates exemplary method steps in fabricating electroactive liquid crystal based lens elements in a tabular form.

FIGS. 13A-13D illustrate aspects of adjusting alignment of layers involved in fabricating electroactive liquid crystal based lens elements.

DETAILED DESCRIPTION OF THE INVENTION

Glossary

Figure 1:
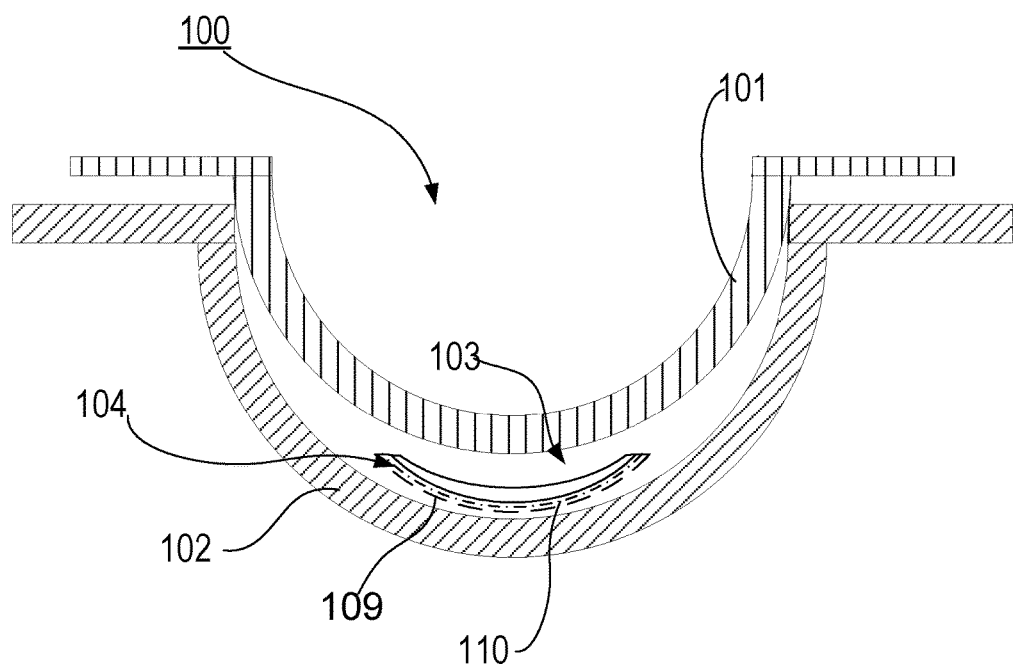
FIG. 1 illustrates exemplary mold assembly apparatus components that may be useful in implementing some embodiments of the present invention.

In this description and claims directed to the presented invention, various terms may be used for which the following definitions will apply:

Alignment layer: as used herein refers to a layer adjacent to a liquid crystal layer that influences and aligns the orientation of molecules within the liquid crystal layer. The resulting alignment and orientation of the molecules may affect light that passes through the liquid crystal layer. For example, the alignment and orientation may act with refractive characteristics upon the incident light. Additionally, the effect may include alteration of the polarization of the light.

Electrical Communication: as used herein refers to being influenced by an electrical field. In the case of conductive materials, the influence may result from or in the flow of electrical current. In other materials, it may be an electrical potential field that causes an influence, such as the tendency to orient permanent and induced molecular dipoles along field lines as an example.

Energized: as used herein refers to the state of being able to supply electrical current to or to have electrical energy stored within.

Energized orientation: as used herein refers to the orientation of the molecules of a liquid crystal when influenced by an effect of a potential field powered by an energy source. For example, a device containing liquid crystals may have one energized orientation if the energy source operates as either on or off. In other embodiments, the energized orientation may change along a scale affected by the amount of energy applied.

Energy: as used herein refers to the capacity of a physical system to do work. Many uses within the present invention may relate to the capacity being able to perform electrical actions in doing work.

Energy source: as used herein refers to device capable of supplying energy or placing a biomedical device in an energized state.

Energy Harvesters: as used herein refers to devices capable of extracting energy from the environment and convert it to electrical energy.

Intraocular lens: as used herein refers to an ophthalmic lens that is embedded within the eye.

Lens-Forming Mixture or Reactive Mixture or Reactive Monomer Mixture (RMM): as used herein refers to a monomer or prepolymer material that can be cured and crosslinked or crosslinked to form an ophthalmic lens. Various embodiments may include lens-forming mixtures with one or more additives, such as UV blockers, tints, photoinitiators or catalysts, and other additives one might desire in an ophthalmic lens, for example, contact or intraocular lenses.

Lens-Forming Surface: as used herein refers to a surface that is used to mold a lens. In some embodiments, any such surface may have an optical quality surface finish, which indicates that it is sufficiently smooth and formed so that a lens surface fashioned by the polymerization of a lens-forming mixture in contact with the molding surface is optically acceptable. Further, in some embodiments, the lens-forming surface may have a geometry that is necessary to impart to the lens surface the desired optical characteristics, including, for example, spherical, aspherical and cylinder power, wave front aberration correction, and corneal topography correction.

Liquid Crystal: as used herein refers to a state of matter having properties between a conventional liquid and a solid crystal. A liquid crystal cannot be characterized as a solid but its molecules exhibit some degree of alignment. As used herein, a liquid crystal is not limited to a particular phase or structure, but a liquid crystal may have a specific resting orientation. The orientation and phases of a liquid crystal may be manipulated by external forces, for example, temperature, magnetism, or electricity, depending on the class of liquid crystal.

Lithium Ion Cell: as used herein refers to an electrochemical cell where Lithium ions move through the cell to generate electrical energy. This electrochemical cell, typically called a battery, may be reenergized or recharged in its typical forms.

Media insert or insert: as used herein refers to a formable or rigid substrate capable of supporting an energy source within an ophthalmic lens. In some embodiments, the media insert also includes one or more variable optic portions.

Mold: as used herein refers to a rigid or semi-rigid object that may be used to form lenses from uncured formulations. Some preferred molds include two mold parts forming a front curve mold part and a back curve mold part.

Ophthalmic Lens or Lens: as used herein refers to any ophthalmic device that resides in or on the eye. These devices can provide optical correction or may be cosmetic. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. In some embodiments, the preferred lenses of the invention are soft contact lenses which are made from silicone elastomers or hydrogels, which include, for example, silicone hydrogels and fluorohydrogels.

Optical zone: as used herein refers to an area of an ophthalmic lens through which a wearer of the ophthalmic lens sees.

Power: as used herein refers to work done or energy transferred per unit of time.

Rechargeable or Reenergizable: as used herein refers to a capability of being restored to a state with higher capacity to do work. Many uses within the present invention may relate to the capability of being restored with the ability to flow electrical current at a certain rate for a certain time period.

Reenergize or Recharge: as used herein refers to the restoration of an energy source to a state with higher capacity to do work. Many uses within the present invention may relate to restoring a device to the capability to flow electrical current at a certain rate for a certain time period.

Released from a mold: as used herein refers to a lens is either completely separated from the mold, or is only loosely attached so that it may be removed with mild agitation or pushed off with a swab.

Resting orientation: as used herein refers to the orientation of the molecules of a liquid crystal device in its resting, non-energized state.

Variable optic: as used herein refers to the capacity to change an optical quality, for example, the optical power of a lens or the polarizing angle.

Fabricating LC Lenses

The present invention includes methods and apparatuses for manufacturing an ophthalmic lens with a variable optic insert wherein the variable optic portion comprises a liquid crystal or a composite material which itself includes liquid crystal constituents. In addition, the present invention includes an ophthalmic lens with a variable optic insert comprising liquid crystal incorporated into the ophthalmic lens.

According to the present invention, an ophthalmic lens is formed with an embedded insert and an energy source, such as an electrochemical cell or battery as the storage means for the energy. In some exemplary embodiments, the materials comprising the energy source may be encapsulated and isolated from an environment into which an ophthalmic lens is placed. In some exemplary embodiments the energy source may include alkaline electrochemical cell chemistry which may be used in a primary or rechargeable configuration.

A wearer-controlled adjustment device may be used to vary the optic portion. The adjustment device may include, for example, an electronic device or passive device for increasing or decreasing a voltage output or engaging and disengaging the energy source. Some exemplary embodiments may also include an automated adjustment device to change the variable optic portion via an automated apparatus according to a measured parameter or a wearer input. Wearer input may include, for example, a switch controlled by wireless apparatus. Wireless may include, for example, radio frequency control, magnetic switching, patterned emanations of light, and inductance switching. In other exemplary embodiments activation may occur in response to a biological function or in response to a measurement of a sensing element within the ophthalmic lens. Other exemplary embodiments may result from the activation being triggered by a change in ambient lighting conditions as a non-limiting example.

Variation in optic power may occur when electric fields, created by the energization of electrodes, causes realignment within the liquid crystal layer thereby shifting the molecules from the resting orientation to an energized orientation. In other alternative exemplary embodiments, different effects caused by the alteration of liquid crystal layers by energization of electrodes may be exploited, for example, changing of the light polarization state, particularly, polarization rotation.

In some exemplary embodiments with liquid crystal layers, there may be elements in the non-optical zone portion of the ophthalmic lens that may be energized, whereas other exemplary embodiments may not require energization. In the exemplary embodiments without energization, the liquid crystal may be passively variable based on some exterior factor, such as, for example, ambient temperature, or ambient light.

A liquid crystal lens may provide an electrically variable index of refraction to polarized light incident upon its body. A combination of two lenses where the optical axis orientation is rotated in the second lens relative to the first lens allows for a lens element that may be able to vary the index of refraction to ambient non-polarized light.

By combining electrically active liquid crystal layers with electrodes, a physical entity may derive that may be controlled by applying an electrical field across the electrodes. If there is a dielectric layer that is present on the periphery of the liquid crystal layer then the field across the dielectric layer and the field across the liquid crystal layer may combine into the field across the electrodes. In a three dimensional shape the nature of the combination of the fields across the layers may be estimated based on electrodynamic principals and the geometry of the dielectric layer and the liquid crystal layer. If the effective electrical thickness of the dielectric layer is made in a non-uniform manner then the effect of a field across the electrodes may be "shaped" by the effective shape of the dielectric and create dimensionally shaped changes in refractive index in the liquid crystal layers. In some exemplary embodiments, such shaping may result in lenses that have the ability to adopt variable focal characteristics.

An alternative exemplary embodiment may derive when the physical lens elements that contain the liquid crystal layers are shaped themselves to have different focal characteristics. The electrically variable index of refraction of a liquid crystal layer may then be used to introduce changes in focal characteristics of the lens based on the application of an electric field across the liquid crystal layer through the use of electrodes. The index of refraction of a liquid crystal layer may be referred to as an effective index of refraction, and it may be possible to consider each treatment relating to an index of refraction as equivalently referring to an effective index of refraction. The effective index of refraction may come, for example, from the superposition of multiple regions with different index of refraction. In some exemplary embodiments, the effective aspect may be an average of the various regional contributions, in other exemplary embodiments the effective aspect may be a superposition of the regional or molecular effects upon incident light. The shape that the front containment surface makes with the liquid crystal layer and the shape that the back containment surface makes with the liquid crystal layer may determine to first order the focal characteristics of the system.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

Ophthalmic Lenses

Referring to FIG. 1, an apparatus 100 to form ophthalmic devices containing sealed and encapsulated inserts is depicted. The apparatus 100 includes an exemplary front curve mold such as mold part 102 and a matching back curve mold 101. A variable optic insert 104 and a body 103 of the ophthalmic device may be located inside the front curve mold, mold part 102 and the back curve mold 101. In some exemplary embodiments, the material of the body 103 may be a hydrogel material, and the variable optic insert 104 may be surrounded on all surfaces by this material.

The variable optic insert 104 may comprise multiple liquid crystal layers 109 and 110. Other exemplary embodiments may include a single liquid crystal layer, some of which are discussed in later sections. The use of the apparatus 100 may create a novel ophthalmic device comprising a combination of components with numerous sealed regions.

In some exemplary embodiments, a lens with a variable optic insert 104 may include a rigid center soft skirt design, wherein a central rigid optical element including the liquid crystal layers 109 and 110 is in direct contact with the atmosphere and the corneal surface on respective anterior and posterior surfaces. The soft skirt of lens material (typically a hydrogel material) is attached to a periphery of the rigid optical element, and the rigid optical element may also add energy and functionality to the resulting ophthalmic lens.

Figure 2A:
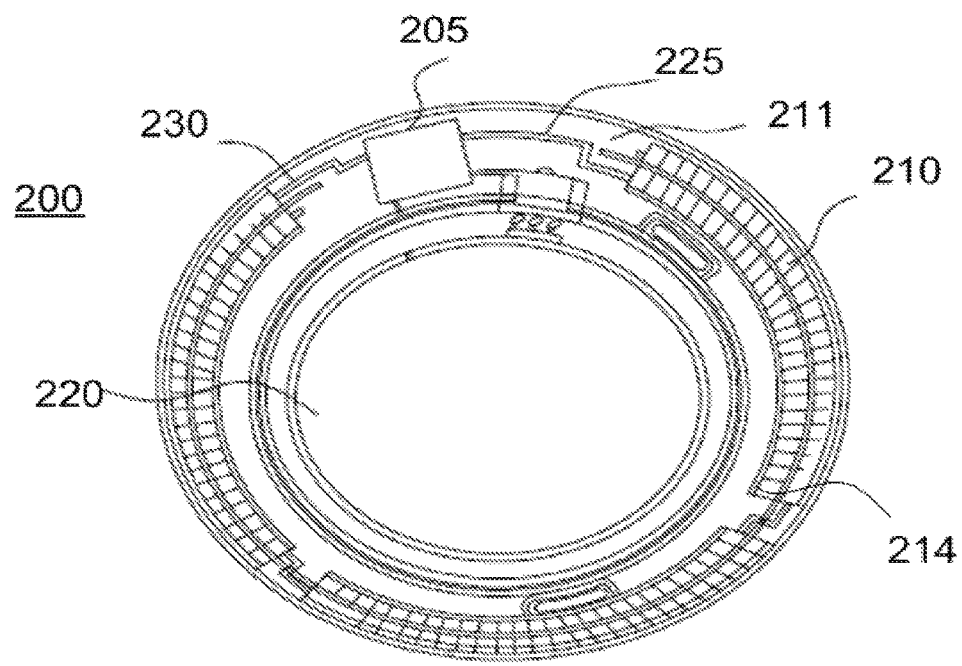
FIGS. 2A and 2B illustrates an exemplary energized ophthalmic lens with a variable optic insert embodiment.
Figure 2B:
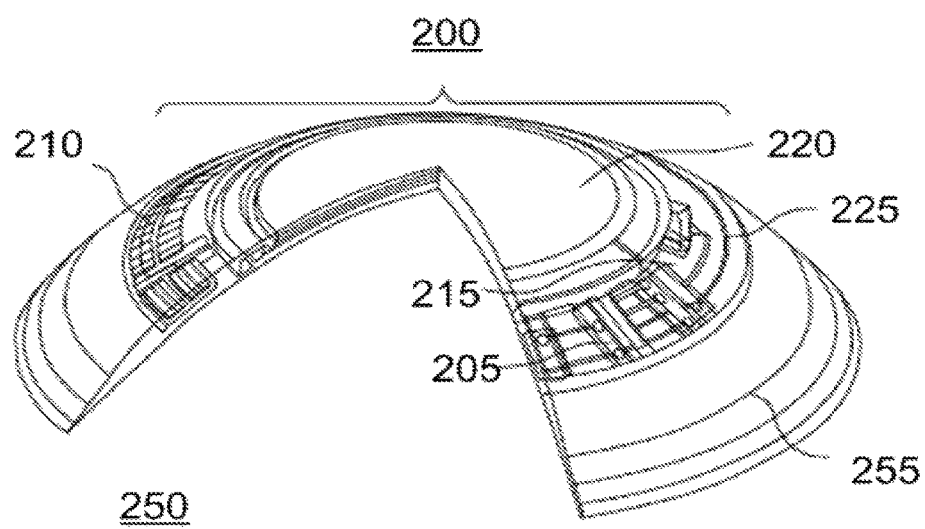

Referring to FIG. 2A, at 200 a top down and FIG. 2B at 250 a cross sectional depiction of an exemplary embodiment of a variable optic insert is shown. In this depiction, an energy source 210 is shown in a periphery portion 211 of the variable optic insert 200. The energy source 210 may include, for example, a thin film, rechargeable lithium ion battery or an alkaline cell based battery. The energy source 210 may be connected to interconnect features 214 to allow for interconnection. Additional interconnects at 225 and 230, for example, may connect the energy source 210 to an electronic circuit 205. In other exemplary embodiments, an insert may have interconnect features deposited on its surface.

In some exemplary embodiments, the variable optic insert 200 may include a flexible substrate. This flexible substrate may be formed into a shape approximating a typical lens form in a similar manner previously discussed or by other means. However, to add additional flexibility, the variable optic insert 200 may include additional shape features such as radial cuts along its length. There may be multiple electronic components such as that indicated by 205 such as integrated circuits, discrete components, passive components and such devices that may also be included.

A variable optic portion 220 is also illustrated. The variable optic portion 220 may be varied on command through the application of a current through the variable optic insert which in term may typically vary an electric field established across a liquid crystal layer. In some exemplary embodiments, the variable optic portion 220 comprises a thin layer of liquid crystal between two layers of transparent substrate. There may be numerous manners of electrically activating and controlling the variable optic component, typically through action of the electronic circuit 205. The electronic circuit 205 may receive signals in various manners and may also connect to sensing elements which may also be in the insert such as item 215. In some exemplary embodiments, the variable optic insert may be encapsulated into a lens skirt 255, which may comprise a hydrogel material or other suitable material to form an ophthalmic lens. In these exemplary embodiments the ophthalmic lens may comprise the lens skirt 255 and an encapsulated variable optic insert 200 which may itself comprise layers or regions of liquid crystal material or comprising liquid crystal material.

A Variable Optic Insert Including Liquid Crystal Elements

Figure 3:
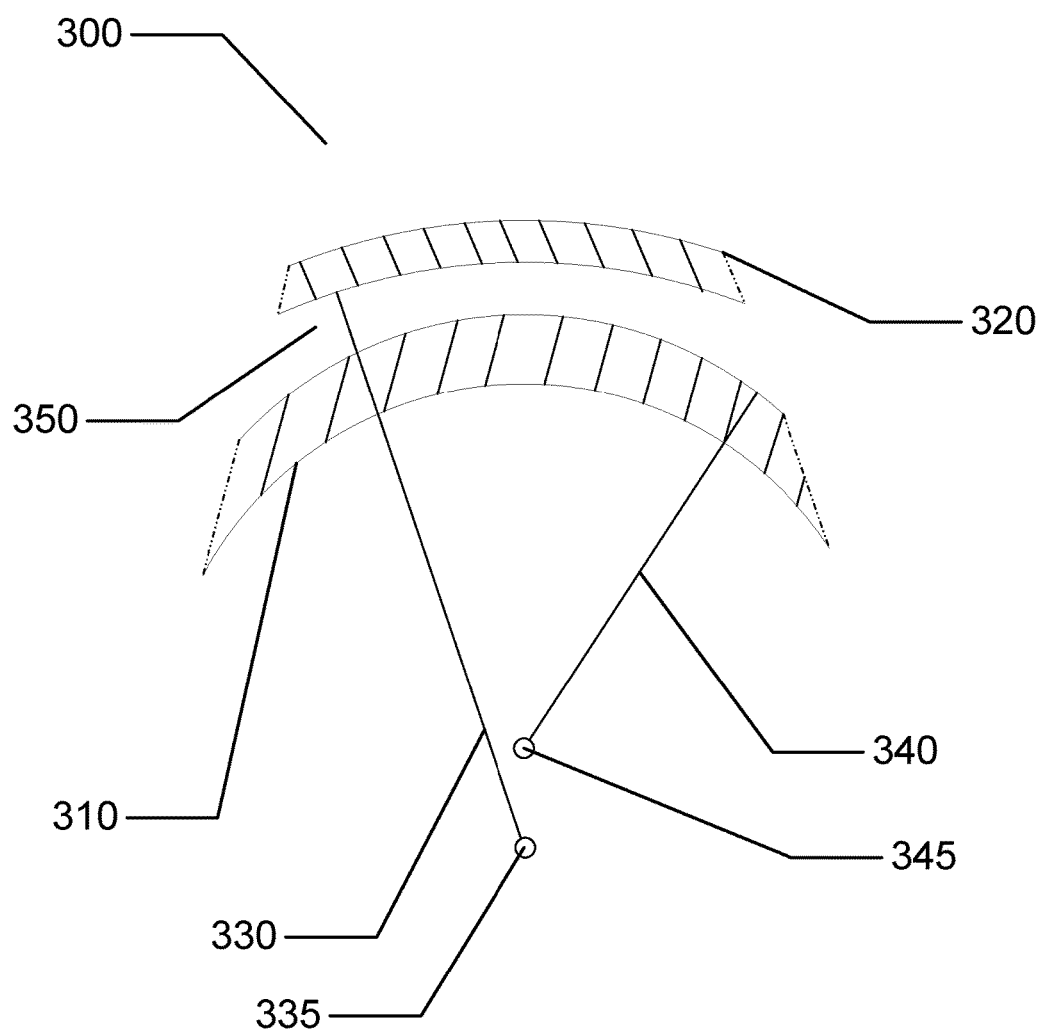
FIG. 3 illustrates a cross sectional view of a variable optic insert where the front and back curve pieces of the variable optic insert may have different curvature and wherein the variable optic portion may be comprised of liquid crystal.

Referring to FIG. 3, item 300, an illustration of the lens effect of two differently shaped lens pieces may be found. As mentioned previously, a variable optic insert of the inventive art herein may be formed by enclosing an electrode and liquid crystal layer system within two differently shaped lens pieces. The electrode and liquid crystal layer system may occupy a space between the lens pieces as illustrated at 350. At 320 a front curve piece may be found and at 310 a rear curve piece may be found.

In a non-limiting example, the front curve piece 320 may have a concave shaped surface that interacts with the space 350. The shape may be further characterized as having a radius of curvature depicted as 330 and a focal point 335 in some embodiments. Other more complicated shapes with various parametric characteristics may be formed within the scope of the inventive art; however, for illustration a simple spherical shape may be depicted.

In a similar and also non-limiting fashion, the back curve piece 310 may have a convex shaped surface that interacts with the space 350. The shape may be further characterized as having a radius of curvature depicted as 340 and a focal point 345 in some embodiments. Other more complicated shapes with various parametric characteristics may be formed within the scope of the inventive art; however, for illustration a simple spherical shape may be depicted.

To illustrate how the lens of the type as 300 may operate, the material that comprises lens pieces: back curve piece 310 and front curve piece 320 may have an index of refraction of a value n. Within the space 350, the liquid crystal composite material layer may be chosen in a non-limiting example to match that value for the index of refraction. Thus when light rays traverse the lens pieces: back curve piece 310 and front curve piece 320 and the space 350, they will not react to the various interfaces in a manner that would adjust the focal characteristics. In its function, portions of the lens not shown may activate an energization of various components that may result in the liquid crystal layer in space 350 assuming a different index of refraction to the incident light ray. In a non-limiting example, the resulting index of refraction may be lowered or raised. Now, at each material interface, the path of the light may be modeled to be altered based on the focal characteristics of the surface and the change of the index of refraction.

The model may be based on Snell's law: sin (theta$_1$)/sin (theta$_2$)=n$_2$/n$_1$. For example, the interface may be formed by front curve piece 320 and space 350, theta$_1$ may be the angle that the incident ray makes with a surface normal at the interface. Theta$_2$ may be the modeled angle that the ray makes with a surface normal as it leaves the interface. n$_2$ may represent the index of refraction of the space 350 and n$_1$ may represent the index of refraction of the front curve piece 320. When n$_1$ is not equal to n$_2$ then the angles theta$_1$ and theta$_2$ will be different as well. Thus, when the electrically variable index of refraction of the liquid crystal layer in space 350 is changed, the path that a light ray would take at the interface will change as well.

Figure 4:
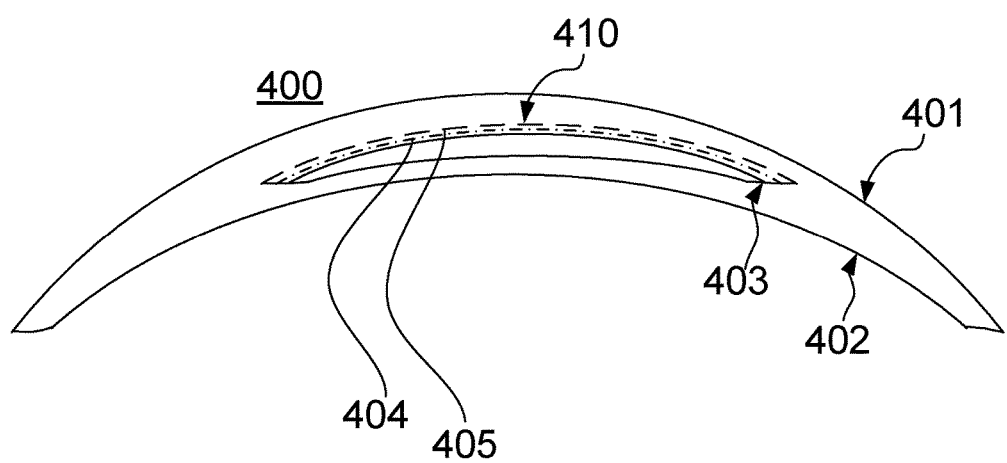
FIG. 4 illustrates a cross sectional view of an ophthalmic lens device embodiment with a variable optic insert wherein the variable optic portion may be comprised of liquid crystal.

Referring to FIG. 4, an ophthalmic lens 400 is shown with an embedded variable optic insert, insert 410. The ophthalmic lens 400 may have a front curve surface 401 and a back curve surface 402. The insert 410 may have a variable optic portion 403 with a liquid crystal layer 404. In some exemplary embodiments, the insert 410 may have multiple liquid crystal layers 404 and 405. Portions of the insert 410 may overlap with the optical zone of the ophthalmic lens 400.

Figure 5:
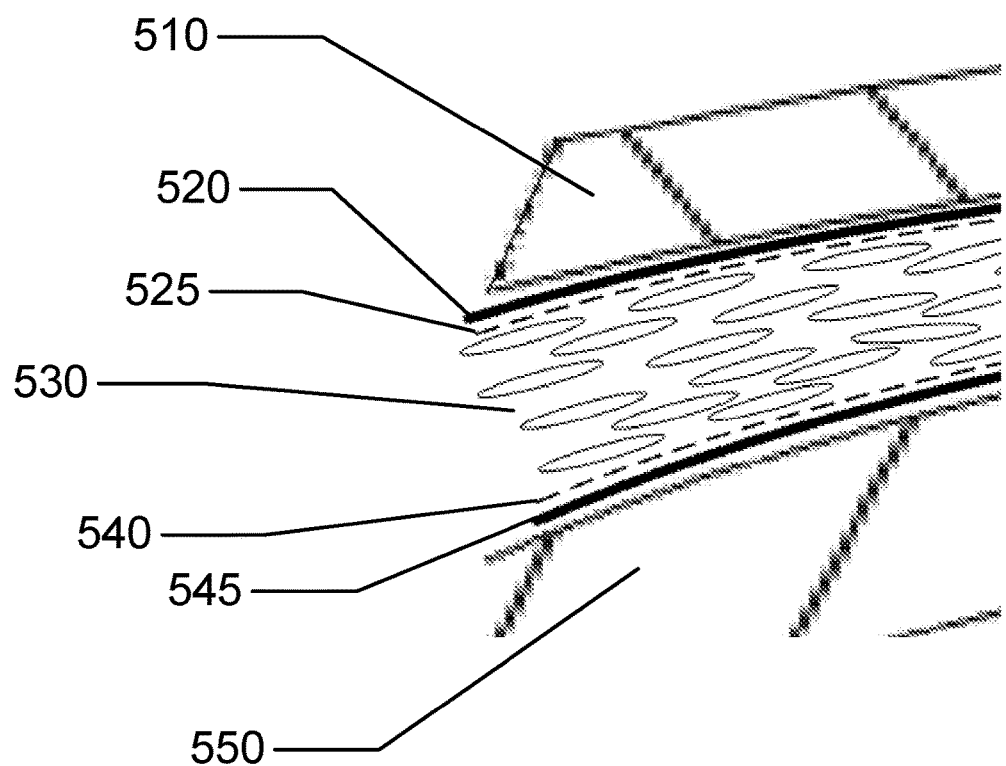
FIG. 5 illustrates an exemplary embodiment or a variable optic insert wherein the variable optic portion may be comprised of liquid crystal.

Referring to FIG. 5, a variable optic portion 500 that may be inserted into an ophthalmic lens is illustrated with a liquid crystal layer 530. The variable optic portion 500 may have a similar diversity of materials and structural relevance as has been discussed in other sections of this specification. In some exemplary embodiments, a transparent electrode 545 may be placed on a first transparent substrate 550. The first lens surface or alignment layer 540 may comprise a dielectric film, and in some exemplary embodiments, alignment layers which may be placed upon the first transparent electrode 545. In such exemplary embodiments, the shape of the dielectric layer of the first lens surface may form a regionally varied shape in the dielectric thickness as depicted. Such a regionally varied shape may introduce additional focusing power of the lens element above the geometric effects discussed in reference to FIG. 3. In still further exemplary embodiments, the shaped layer may be formed by injection molding upon the first transparent electrode 545 first transparent substrate 550 combination.

In some exemplary embodiments the first transparent electrode 545 and a second transparent electrode 520 may be shaped in various manners. In some examples, the shaping may result in separate and distinct regions being formed that may have energization applied separately. In other examples, the electrodes may be formed into patterns such as a helix from the center of the lens to the periphery which may apply a variable electric field across the liquid crystal layer 530. In either case, such electrode shaping may be performed in addition to the shaping of dielectric layer upon the electrode or instead of such shaping. The shaping of electrodes in these manners may also introduce additional focusing power of the lens element under operation.

The liquid crystal layer 530 may be located between the first transparent electrode 545 and the second transparent electrode 520. The second transparent electrode 520 may be deposited on a second transparent substrate 510, wherein the device formed from the second transparent substrate 510 to the first transparent substrate 550 may contain the variable optic portion 500 of the ophthalmic lens. Two alignment layers may also be located at 540 and 525 upon the dielectric layer and may surround the liquid crystal layer 530. The alignment layers at 540 and 525 may function to define a resting orientation of the ophthalmic lens. In some exemplary embodiments, the transparent electrode layers 520 and 545 may be in electrical communication with liquid crystal layer 530 and cause a shift in orientation from the resting orientation to at least one energized orientation.

Figure 6A:
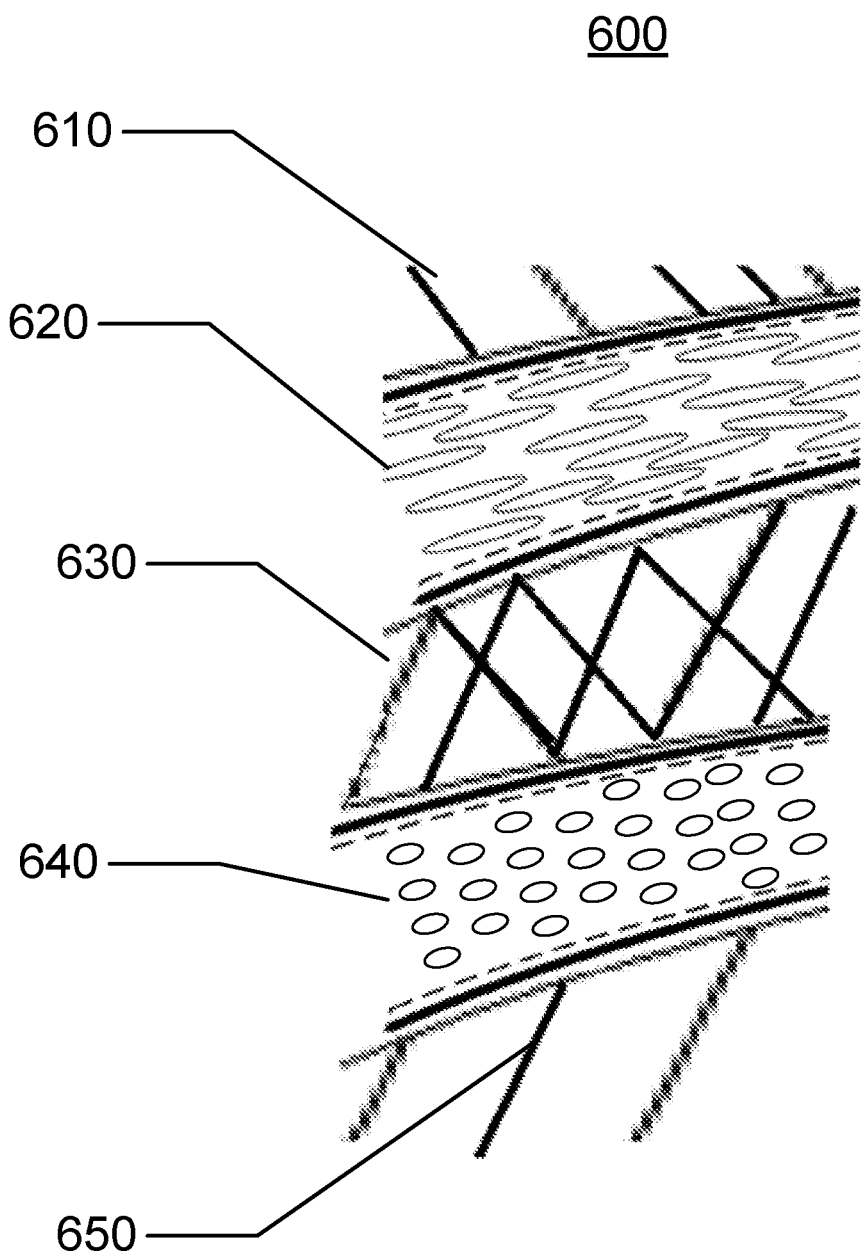
FIG. 6A illustrates an alternative embodiment of a variable optic insert wherein the variable optic portions may be comprised of liquid crystal.

Referring to FIG. 6A, an alternative of a variable optic insert 600 that may be inserted into an ophthalmic lens is illustrated with two liquid crystal layers 620 and 640. Each of the aspects of the various layers around the liquid crystal region may have similar diversity as described in relation to the variable optic portion 500 illustrated in FIG. 5. In some exemplary embodiments, the alignment layers may introduce polarization sensitivity into the function of a single liquid crystal element. By combining a first liquid crystal based element formed by a first substrate 610, whose intervening layers in the space around 620 and a second substrate 630 may have a first polarization preference, with a second liquid crystal based element formed by a second surface on the second substrate 630, the intervening layers in the space around 640 and a third substrate 650 with a second polarization preference, a combination may be formed which may allow for an electrically variable focal characteristic of a lens that is not sensitive to the polarization aspects of incident light upon it.

At the exemplary variable optic insert 600, a combination of two electrically active liquid crystal layers of the various types and diversity associated with the example at 500 may be formed utilizing three substrate layers. In other examples, the device may be formed by the combination of four different substrates. In such examples, the intermediate substrate or second substrate 630 may be split into two layers. If the substrates are combined at a later time, a device that functions similarly to variable optic insert 600 may result. The combination of four layers may present a convenient example for the manufacturing of the element where similar devices may be constructed around both 620 and 640 liquid crystal layers where the processing difference may relate to the portion of steps that define alignment features for the liquid crystal element. In still further examples, if the lens element around a single liquid crystal layer such that is depicted at 500 is spherically symmetric or symmetric upon a rotation of ninety degrees, then two pieces may be assembled into a structure of the type depicted at 600 by rotating the two pieces ninety degrees relative to each other before assembling.

Figure 6B:
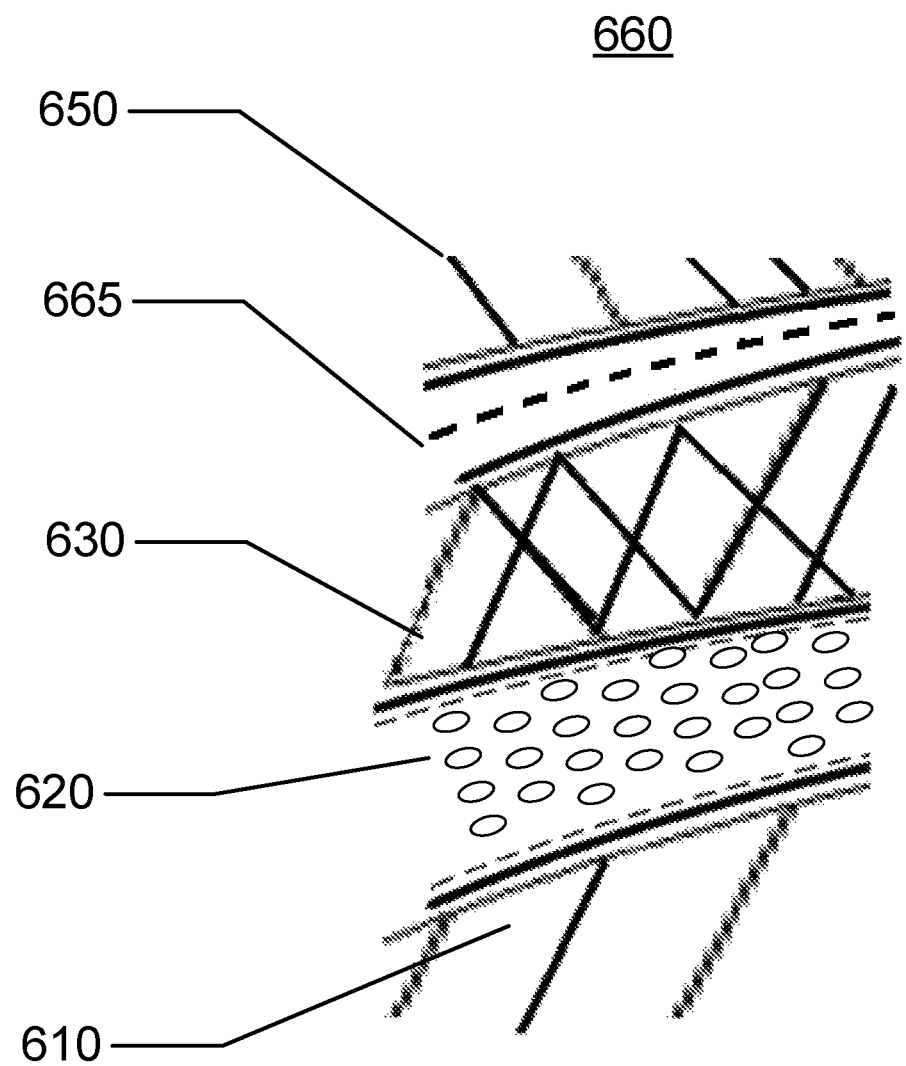
FIG. 6B illustrates an alternative embodiment of a variable optic insert wherein the variable optic portions may be comprised of liquid crystal and the insert also may comprise a polarizing element.

An alternative exemplary embodiment which is not sensitive to the polarization aspects of incident light upon it may be found in reference to FIG. 6B at item 660. In the embodiment at 660, a single optical element of the type referred to in discussions relating to FIG. 5 may be found with first and second substrates at 610 and 630 respectively surrounding an active liquid crystal later comprising liquid crystal elements at 620. As mentioned the aligned liquid crystal elements may act differently upon the different polarization components of incident light. Instead of combining two orthogonally deployed aligned liquid crystal layers; however, a polarizing filter 665 may be located as illustrated in FIG. 6B. In some exemplary embodiments, the polarizing filter 665 may allow the polarized light consistent with the alignment of liquid crystal layer 620 to pass through it while blocking the orthogonal polarization component. Therefore, the electrically active focal aspects of the liquid crystal layer 620 may create a single effect on incident light upon the lens; albeit for one polarization component of the incident light.

The embodiment of 660 in FIG. 6B depicts a polarizing filter at 665, which in some embodiments may be static or in other embodiments may be electrically active. This layer may, in an exemplary manner, be located between two insert pieces for containment. Such an exemplary embodiment, may be found in FIG. 6B as the polarization filter 665 may be located between a second substrate 630 and a third substrate 650. There may be many embodiments relating to the use of a polarizing element in an aligned liquid crystal containing optical device, including in a non-limiting sense, where the polarization element is created upon either of the first or second insert pieces without being between two insert pieces. Alternatively, both the liquid crystal layer 620 and an associated polarization filter 665 may together be located between a first and second insert piece for example.

Figure 6C:
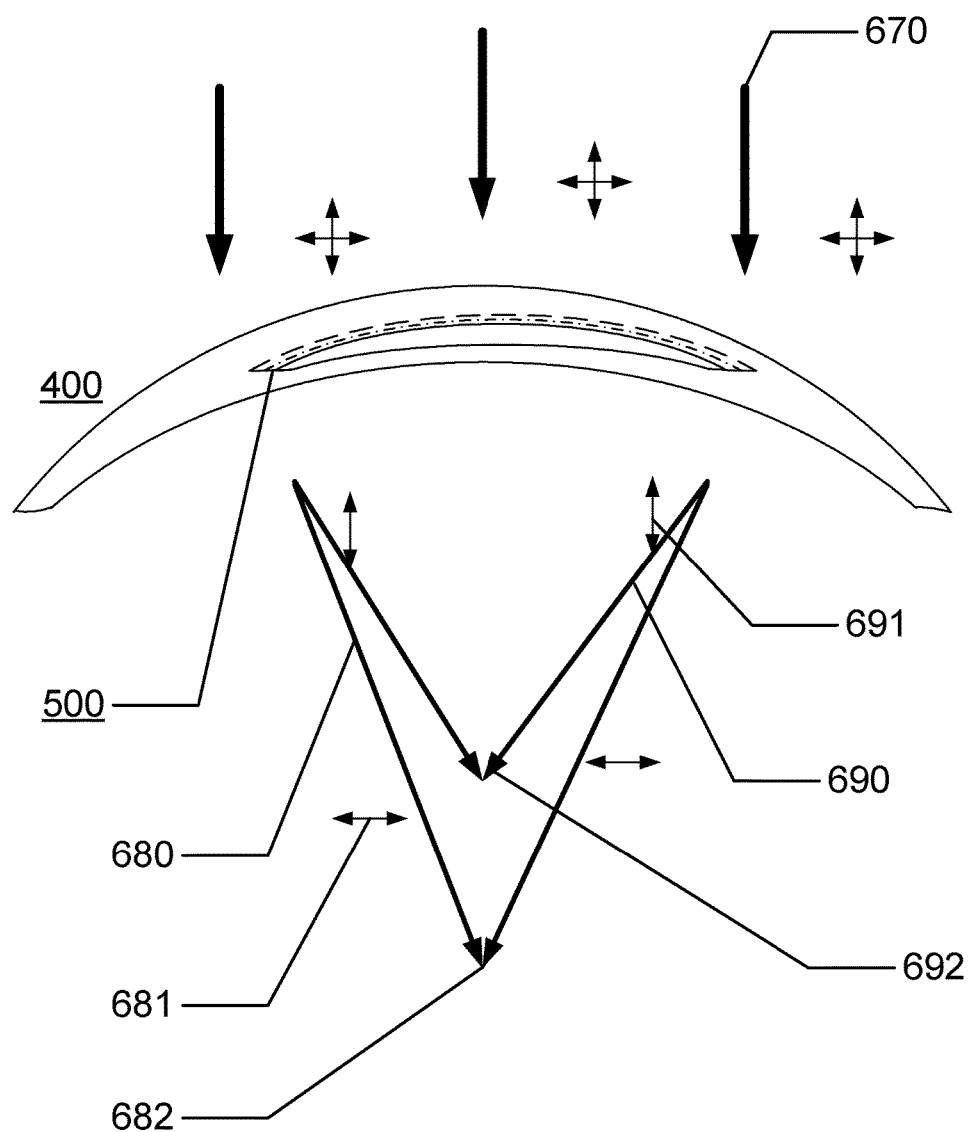
FIG. 6C illustrates an alternative exemplary embodiment of a variable optic insert wherein the variable optic portion may be comprised of liquid crystal and the manner that polarized light components may be affected while traversing the embodiment.

Bifocal Ophthalmic Devices Comprising Single Polarization Sensitive Liquid Crystal Layers with Active and Passive Aspects Referring to FIG. 6C, a different class of devices may result from forming an ophthalmic device with liquid crystal layers. In the embodiments related to the devices illustrated in FIGS. 6A and 6B, the property that a single layer of aligned liquid crystal layers reacts differently for different polarization components of incident light was exploited in different manners to create devices that deliver a single optical or focal aspect of light to a user's retina. In the different class of devices relating to FIG. 6C the fact that a single aligned layer of liquid crystal material acts on different polarization components of incident light in a different manner defines part of the ophthalmic device function. Such a device may be characterized to be a type of bifocal ophthalmic device comprising single polarization sensitive liquid crystal layers. An ophthalmic lens 400 of the type described in FIG. 4, may be provided with an insert having a variable optic portion 500 comprising a liquid crystal layer. The layer of the various types that have been described may be aligned by alignment layers and therefore have a sensitivity to a particular polarization state. If the device has a focal adjusting function and has a single aligned liquid crystal layer, or alternatively is a dual layer device, where one liquid crystal layer is aligned in an orthogonal direction to the other liquid crystal layer, and one of the liquid crystal layers is electrically energized to a different level than the other, then the light 670 incident upon the ophthalmic lens 400 may be resolved into two different focal characteristics for each of the polarization directions. As depicted, one of the polarization components 681 may be focused on a path 680 towards a focal point 682 whereas the other polarization component 691 may be focused on a path 690 towards focal point 692.

In state of the art ophthalmic devices there are a class of bifocal devices that simultaneously present multiply focused images to a user's eye. A human's brain may have a capability of sorting out the two images and perceiving the different images. The device at FIG. 6C may deliver such a bifocal capability in a superior manner. Rather than intercepting regions of the global image and focusing them differently, a liquid crystal layer of the type depicted at FIG. 6C may divide the light 670 into two polarization components 681 and 691 across the entire visible window. As long as the incident light 670 does not have a polarization preference then the images should appear similarly as would be the case with either focal characteristic alone. In other exemplary embodiments, such an ophthalmic device may be paired with light sources that are projected with defined polarizations for different effects such as displaying information with a select polarization so that it is brought to the magnified image. Liquid Crystal Displays may inherently provide such an ambient condition since light may emerge from such a display with a defined polarization characteristic. There may be many embodiments that result from the ability to leverage the devices with multiple focal characteristics.

In other exemplary embodiments, the ability to actively control the focus of the device may allow for devices with a range of bifocal conditions. A resting state or non-energized state may comprise a bifocal with one polarization unfocused and the other polarization focused on mid-distances. On activation the mid-distance component may be further focused to near imaging if the lens is bistable, or a range of focal lengths in other embodiments. The bifocal characteristic may allow a user to perceive his distance environment simultaneously with a focused image at various distances, which may have advantages of various kinds.

Materials

Microinjection molding embodiments may include, for example, a poly(4-methylpent-1-ene) copolymer resin are used to form lenses with a diameter of between about 6 mm to 10 mm and a front surface radius of between about 6 mm and 10 mm and a rear surface radius of between about 6 mm and 10 mm and a center thickness of between about 0.050 mm and 1.0 mm. Some exemplary embodiments include an insert with diameter of about 8.9 mm and a front surface radius of about 7.9 mm and a rear surface radius of about 7.8 mm and a center thickness of about 0.200 mm and an edge profile of about 0.050 mm radius.

The variable optic insert 104 of FIG. 1 may be placed in a mold part 101 and 102 utilized to form an ophthalmic lens in FIG. 1. Mold part 101 and 102 material may include, for example, a polyolefin of one or more of: polypropylene, polystyrene, polyethylene, polymethyl methacrylate, and modified polyolefins. Other molds may include a ceramic or metallic material.

A preferred alicyclic co-polymer contains two different alicyclic polymers. Various grades of alicyclic co-polymers may have glass transition temperatures ranging from 105° C. to 160° C.

In some exemplary embodiments, the molds of the invention may include polymers such as polypropylene, polyethylene, polystyrene, polymethyl methacrylate, modified polyolefins containing an alicyclic moiety in the main chain and cyclic polyolefins. This blend may be used on either or both mold halves, where it is preferred that this blend is used on the back curve and the front curve consists of the alicyclic co-polymers.

In some preferred methods of making molds according to the present invention, injection molding is utilized according to known techniques; however, embodiments may also include molds fashioned by other techniques including, for example: lathing, diamond turning, or laser cutting.

Typically, lenses are formed on at least one surface of both mold parts 101 and 102. However, in some embodiments, one surface of a lens may be formed from a mold part 101 or 102 and another surface of a lens may be formed using a lathing method, or other methods.

In some exemplary embodiments, a preferred lens material includes a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some exemplary embodiments, the ophthalmic lens skirt, also called an insert-encapsulating layer, that surrounds the insert may be comprised of standard hydrogel ophthalmic lens formulations. Exemplary materials with characteristics that may provide an acceptable match to numerous insert materials may include the Narafilcon family (including Narafilcon A and Narafilcon B), and the Etafilcon family (including Etafilcon A). A more technically inclusive discussion follows on the nature of materials consistent with the art herein. One ordinarily skilled in the art may recognize that other material other than those discussed may also form an acceptable enclosure or partial enclosure of the sealed and encapsulated inserts and should be considered consistent and included within the scope of the claims.

Suitable silicone containing components include compounds of Formula I

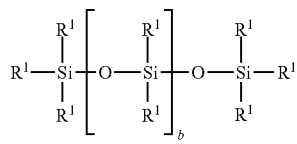

where $R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one exemplary embodiment, b is zero, one $R^1$ is a monovalent reactive group, and at least 3 $R^1$ are selected from monovalent alkyl groups having one to 16 carbon atoms, and in another exemplary embodiment from monovalent alkyl groups having one to 6 carbon atoms. Non-limiting examples of silicone components of this exemplary embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another exemplary embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another exemplary embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another exemplary embodiment, b is 5 to 400 or from 10 to 300, both terminal $R^1$ comprise monovalent reactive groups and the remaining $R^1$ are independently selected from monovalent alkyl groups having 1 to 18 carbon atoms, which may have ether linkages between carbon atoms and may further comprise halogen.

In one exemplary embodiment, where a silicone hydrogel lens is desired, the lens of the present invention will be made from a reactive mixture comprising at least about 20 and preferably between about 20 and 70% wt silicone containing components based on total weight of reactive monomer components from which the polymer is made.

In another exemplary embodiment, one to four $R^1$ comprises a vinyl carbonate or carbamate of the formula:

Formula II

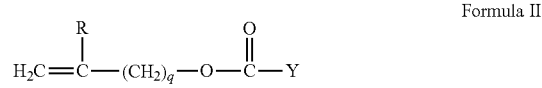

wherein: Y denotes O—, S— or NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris (trimethylsiloxy)silyl] propyl allyl carbamate; 3-[tris (trimethylsiloxy)silyl] propyl vinyl carbamate; trimethylsilylethyl vinyl carbonate; trimethylsilylmethyl vinyl carbonate, and

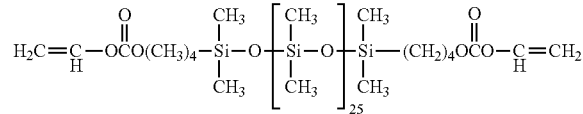

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

(*D*A*D*G)$_a$*D*D*E$^1$;

E(*D*G*D*A)$_a$*D*G*D*E$^1$ or;

E(*D*A*D*G)$_a$*D*A*D*E$^1$    Formulae IV-VI wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;

A denotes a divalent polymeric radical of formula:

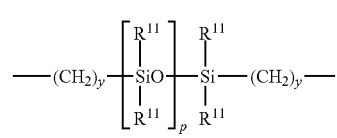

Formula VII $R^{11}$ independently denotes an alkyl or fluoro-substituted alkyl group having 1 to 10 carbon atoms, which may contain ether linkages between carbon atoms; y is at least 1; and p provides a moiety weight of 400 to 10,000; each of E and $E^1$ independently denotes a polymerizable unsaturated organic radical represented by formula:

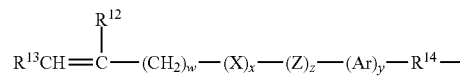

Formula VIII wherein: $R^{12}$ is hydrogen or methyl; $R^{13}$ is hydrogen, an alkyl radical having 1 to 6 carbon atoms, or a —CO—Y— $R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

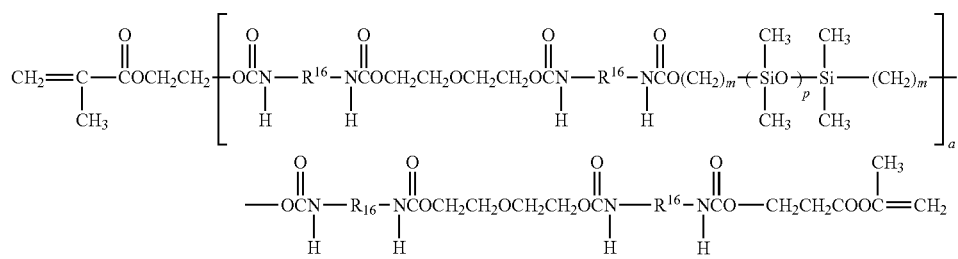

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula X

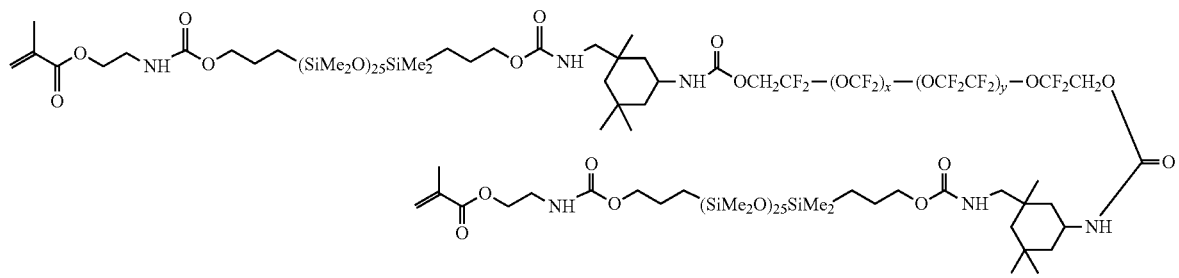

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkages and crosslinkable monomers containing polyether and polysiloxanyl groups. Any of the foregoing polysiloxanes may also be used as the silicone containing component in this invention.

Liquid Crystal Materials

There may be numerous materials that may have characteristics consistent with the liquid crystal layer types that have been discussed herein. It may be expected that liquid crystal materials with favorable toxicity may be preferred and naturally derived cholesteryl based liquid crystal materials may be useful. In other examples, the encapsulation technology and materials of ophthalmic inserts may allow a broad choice of materials that may include the LCD display related materials which may typically be of the broad categories related to nematic or cholesteric N or smectic liquid crystals or liquid crystal mixtures. Commercially available mixtures such as Merck Specialty chemicals Licristal mixtures for TN, VA, PSVA, IPS and FFS applications and other commercially available mixtures may form a material choice to form a liquid crystal layer.

In a non-limiting sense, mixtures or formulations may contain the following liquid crystal materials: 1-(trans-4-Hexylcyclohexyl)-4-isothiocyanatobenzene liquid crystal, benzoic acid compounds including (4-Octylbenzoic acid and 4-Hexylbenzoic acid), carbonitrile compounds including (4'-Pentyl-4-biphenylcarbonitrile, 4'-Octyl-4-biphenylcarbonitrile, 4'-(Octyloxy)-4-biphenylcarbonitrile, 4'-(Hexyloxy)-4-biphenylcarbonitrile, 4-(trans-4-Pentylcyclohexyl) benzonitrile, 4'-(Pentyloxy)-4-biphenylcarbonitrile, 4'-Hexyl-4-biphenylcarbonitrile), and 4,4'-Azoxyanisole.

In a non-limiting sense, formulations showing particularly high birefringence of $n_{par}-n_{perp}>0.3$ at room temperature may be used as a liquid crystal layer forming material. For example, such formulation referred to as W1825 may be as available from AWAT and BEAM Engineering for Advanced Measurements Co. (BEAMCO).

There may be other classes of liquid crystal materials that may be useful for the inventive concepts here. For example, ferroelectric liquid crystals may provide function for electric field oriented liquid crystal embodiments, but may also introduce other effects such as magnetic field interactions. Interactions of electromagnetic radiation with the materials may also differ.

Alignment Layer Materials:

In many of the exemplary embodiments that have been described, the liquid crystal layers within ophthalmic lenses may need to be aligned in various manners at insert boundaries. The alignment, for example, may be parallel or perpendicular to the boundaries of the inserts, and this alignment may be obtained by proper processing of the various surfaces. The processing may involve coating the substrates of the inserts that contain the liquid crystal (LC) by alignment layers. Those alignment layers are described herein.

A technique commonly practiced in liquid crystal based devices of various types may be the rubbing technique. This technique may be adapted to account for the curved surfaces such as the ones of the insert pieces used for enclosing the liquid crystal. In an example, the surfaces may be coated by a polyvinyl alcohol (PVA) layer. For example, a PVA layer may be spin coated using a 1 wt. % aqueous solution. The solution may be applied with spin coating at 1000 rpm for time such as approximately 60 s, and then dried. Subsequently, the dried layer may then be rubbed by a soft cloth. In a non-limiting example, the soft cloth may be velvet.

Photo-alignment may be another technique for producing alignment layers upon liquid crystal enclosures. In some exemplary embodiments, photo-alignment may be desirable due to its non-contact nature and the capability of large scale fabrication. In a non-limiting example, the photo-alignment layer used in the liquid crystal variable optic portion may comprise a dichroic azobenzene dye (azo dye) capable of aligning predominantly in the direction perpendicular to the polarization of linear polarized light of typically UV wavelengths. Such alignment may be a result of repetitive trans-cis-trans photoisomerization processes.

As an example, PAAD series azobenzene dyes may be spin coated from a 1 wt. % solution in DMF at 3000 rpm for 30 s. Subsequently, the obtained layer may be exposed to a linear polarized light beam of a UV wavelength (such as for example, 325 nm, 351 nm, 365 nm) or even a visible wavelength (400-500 nm). The source of the light may take various forms. In some exemplary embodiments, light may originate from laser sources for example. Other light sources, such as LEDs, halogen and incandescent sources may be other non-limiting examples. Either before or after the various forms of light are polarized in the various patterns as appropriate, the light may be collimated in various manners such as through the use of optical lensing devices. Light from a laser source may inherently have a degree of collimation, for example.

A large variety of photoanisotropic materials are known currently, based on azobenzene polymers, polyesthers, photo-crosslinkable polymer liquid crystals with mesogenic 4-(4-methoxycinnamoyloxy)biphenyl side groups and the like. Examples of such materials include sulfonic bisazodye SD1 and other azobenzene dyes, particularly, PAAD-series materials available from BEAM Engineering for Advanced Measurements Co. (BEAMCO), Poly(vinyl cinnamates), and others.

In some exemplary embodiments, it may be desirable to use water or alcohol solutions of PAAD series azo dyes. Some azobenzene dyes, for example, Methyl Red, may be used for photoalignment by directly doping a liquid crystal layer. Exposure of the azobenzene dye to a polarized light may cause diffusion and adhesion of the azo dyes to and within the bulk of the liquid crystal layer to the boundary layers creating desired alignment conditions.

Azobenzene dyes such as Methyl Red may also be used in combination with a polymer, for example, PVA. Other photoanisotropic materials capable of enforcing alignment of adjacent layers of liquid crystals may be acceptable are known currently. These examples may include materials based on coumarines, polyesthers, photo-crosslinkable polymer liquid crystals with mesogenic 4-(4-methoxycinnamoyloxy)-biphenyl side groups, Poly(vinyl cinnamates), and others. The photo-alignment technology may be advantageous for embodiments comprising patterned orientation of liquid crystal.

In another exemplary embodiment of producing alignment layers, the alignment layer may be obtained by vacuum deposition of silicon oxide on the insert piece substrates. For example, $SiO_2$ may be deposited at low pressure such as ~$10^{-6}$ mbar. It may be possible to provide alignment features at a nano-scaled size that are injection molded into with the creation of the front and back insert pieces. These molded features may be coated in various manners with the materials that have been mentioned or other materials that may directly interact with physical alignment features and transmit the alignment patterning into alignment orientation of liquid crystal molecules.

Ion beam alignment may be another technique for producing alignment layers upon liquid crystal enclosures. In some exemplary embodiments, collimated argon ion or focused gallium ion beam may be bombarded upon the alignment layer at a defined angle/orientation. This type of alignment may also be used to align silicon oxide, diamond-like-carbon (DLC), polyimide and other alignment materials.

Still further exemplary embodiments may relate to the creation of physical alignment features to the insert pieces after they are formed. Rubbing techniques as are common in other liquid crystal based art may be performed upon the molded surfaces to create physical grooves. The surfaces may also be subjected to a post molding embossing process to create small grooved features upon them. Still further exemplary embodiments may derive from the use of etching techniques which may involve optical patterning processes of various kinds.

Dielectric Materials

Dielectric films and dielectrics are described herein. By way of non-limiting examples, the dielectric film or dielectrics used in the liquid crystal variable optic portion possess characteristics appropriate to the invention described herein. A dielectric may comprise one or more material layers functioning alone or together as a dielectric. Multiple layers may be used to achieve dielectric performance superior to that of a single dielectric.

The dielectric may permit a defect-free insulating layer at a thickness desired for the discretely variable optic portion, for example, between 1 and 10 µm. A defect may be referred to as a pinhole, as is known by those skilled in the art to be a hole in the dielectric permitting electrical and/or chemical contact through the dielectric. The dielectric, at a given thickness, may meet requirements for breakdown voltage, for example, that the dielectric should withstand 100 volts or more.

The dielectric may allow for fabrication onto curved, conical, spherical, and complex three-dimensional surfaces (e.g., curved surfaces or non-planar surfaces). Typical methods of dip- and spin-coating may be used, or other methods may be employed.

The dielectric may resist damage from chemicals in the variable optic portion, for example, the liquid crystal or liquid crystal mixture, solvents, acids, and bases or other materials that may be present in the formation of the liquid crystal region. The dielectric may resist damage from infrared, ultraviolet, and visible light. Undesirable damage may include degradation to parameters described herein, for example, breakdown voltage and optical transmission. The dielectric may resist permeation of ions. The dielectric may adhere to an underlying electrode and/or substrate, for example, with the use of an adhesion promotion layer. The dielectric may be fabricated using a process which allows for low contamination, low surface defects, conformal coating, and low surface roughness.

The dielectric may possess relative permittivity or a dielectric constant which is compatible with electrical operation of the system, for example, a low relative permittivity to reduce capacitance for a given electrode area. The dielectric may possess high resistivity, thereby permitting a very small current to flow even with high applied voltage. The dielectric may possess qualities desired for an optic device, for example, high transmission, low dispersion, and refractive index within a certain range. Example, non-limiting, dielectric materials, include one or more of Parylene-C, Parylene-HT, Silicon Dioxide, Silicon Nitride, and Teflon AF.

Electrode Materials

Electrodes are described herein for applying an electric potential for achieving an electric field across the liquid crystal region. An electrode generally comprises one or more material layers functioning alone or together as an electrode.

The electrode may adhere to an underlying substrate, dielectric coating, or other objects in the system, perhaps with the use of an adhesion promoter (e.g., methacryloxypropyltrimethoxysilane). The electrode may form a beneficial native oxide or be processed to create a beneficial oxide layer. The electrode may be transparent, substantially transparent or opaque, with high optical transmission and little reflection. The electrode may be patterned or etched with known processing methods. For example, the electrodes may be evaporated, sputtered, or electroplated, using photolithographic patterning and/or lift-off processes.

The electrode may be designed to have suitable resistivity for use in the electrical system described herein, for example, meeting the requirements for resistance in a given geometric construct.

The electrodes may be manufactured from one or more of indium tin oxide (ITO), aluminum doped zinc oxide (AZO), gold, stainless steel, chrome, graphene, graphene doped layers and aluminum. It will be appreciated that this is not an exhaustive list.

Processes

The following method steps are provided as examples of processes that may be implemented according to some aspects of the present invention. It should be understood that the order in which the method steps are presented is not meant to be limiting and other orders may be used to implement the invention. In addition, not all of the steps are required to implement the present invention and additional steps may be included in various embodiments of the present invention. It may be obvious to one skilled in the art that additional embodiments may be practical, and such methods are well within the scope of the claims.

Figure 7:
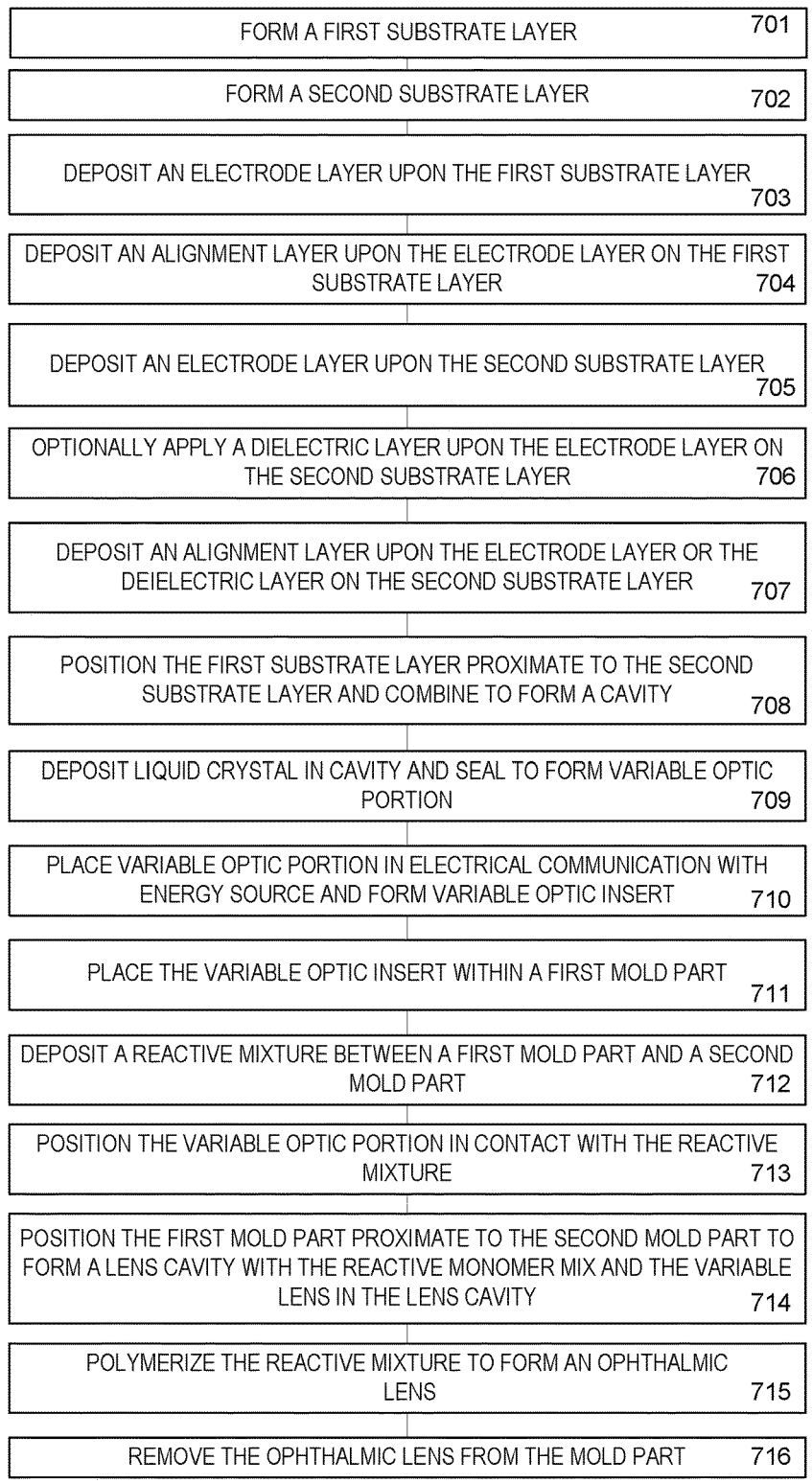
FIG. 7 illustrates method steps for forming an ophthalmic lens with a variable optic insert which may be comprised of liquid crystal.

Referring to FIG. 7, a flowchart illustrates exemplary steps that may be used to implement the present invention. At step 701, a first substrate layer which may comprise a back curve surface and have a top surface with a shape of a first type that may differ from the shape of surface of other substrate layers is formed. In some exemplary embodiments, the difference may include a different radius of curvature of the surface at least in a portion that may reside in the optical zone. At step 702, a second substrate layer which may comprise a front curve surface or an intermediate surface or a portion of an intermediate surface for more complicated devices is formed. At step 703, an electrode layer may be deposited upon the first substrate layer. The deposition may occur, for example, by vapor deposition or electroplating. In some exemplary embodiments, the first substrate layer may be part of an insert that has regions both in the optical zone and regions in the non-optic zone. The electrode deposition process may simultaneously define interconnect features in some exemplary embodiments. In some exemplary embodiments a dielectric layer may be formed upon the interconnects or electrodes. The dielectric layer may comprise numerous insulating and dielectric layers, for example, silicon dioxide.

At step 704, the first substrate layer may be further processed to add an alignment layer upon the previously deposited electrode layer. The alignment layer may be deposited upon the top layer on the substrate and then processed in standard manners, for example, rubbing techniques, to create the grooving features that are characteristic of standard alignment layers or by treatment with exposure to energetic particles or light. Thin layers of photoanisotropic materials may be processed with light exposure to form alignment layers with various characteristics.

At step 705, the second substrate layer may be further processed. An electrode layer may be deposited upon the second substrate layer in an analogous fashion to step 703. Then in some exemplary embodiments, at step 706, a dielectric layer may be applied upon the second substrate layer upon the electrode layer. The dielectric layer may be formed to have a variable thickness across its surface. As an example, the dielectric layer may be molded upon the first substrate layer. Alternatively, a previously formed dielectric layer may be adhered upon the electrode surface of the second substrate piece.

At step 707, an alignment layer may be formed upon the second substrate layer in similar fashion to the processing step at 704. After step 707, two separate substrate layers that may form at least a portion of an ophthalmic lens insert may be ready to be joined. In some exemplary embodiments at step 708, the two pieces will be brought in close proximity to each other and then liquid crystal material may be filled in between the pieces. There may be numerous manners to fill the liquid crystal in between the pieces, including as non-limiting examples, vacuum based filling where the cavity is evacuated and liquid crystal material is subsequently allowed to flow into the evacuated space. In addition, the capillary forces that are present in the space between the lens insert pieces may aid in the filling of the space with liquid crystal material. At step 709, the two pieces may be brought adjacent to each other and then sealed to form a variable optic element with liquid crystal. There may be numerous manners of sealing the pieces together including the use of adhesives, sealants, and physical sealing components such as o-rings and snap lock features as non-limiting examples.

In some exemplary embodiments, two pieces of the type formed at step 709 may be created by repeating method steps 701 to 709 wherein the alignment layers are offset from each other to allow for a lens that may adjust the focal power of non-polarized light. In such embodiments, the two variable optic layers may be combined to form a single variable optic insert. At step 710, the variable optic portion may be connected to the energy source and intermediate or attached components may be placed thereon.

At step 711, the variable optic insert resulting at step 710 may be placed within a mold part. The variable optic insert may or may not also contain one or more components. In some preferred embodiments, the variable optic insert is placed in the mold part via mechanical placement. Mechanical placement may include, for example, a robot or other automation, such as that known in the industry to place surface mount components. Human placement of a variable optic insert is also within the scope of the present invention. Accordingly, any mechanical placement or automation may be utilized which is effective to place a variable optic insert with an energy source within a cast mold part such that the polymerization of a reactive mixture contained by the mold part will include the variable optic in a resultant ophthalmic lens.

In some exemplary embodiments, a variable optic insert is placed in a mold part attached to a substrate. An energy source and one or more components are also attached to the substrate and are in electrical communication with the variable optic insert. Components may include, for example, circuitry to control power applied to the variable optic insert. Accordingly, in some exemplary embodiments a component includes control mechanism for actuating the variable optic insert to change one or more optical characteristics, such as, for example, a change of state between a first optical power and a second optical power.

In some exemplary embodiments, a processor device, MEMS, NEMS or other component may also be placed into the variable optic insert and in electrical contact with the energy source. At step 712, a reactive monomer mixture may be deposited into a mold part. At step 713, the variable optic insert may be positioned into contact with the reactive mixture. In some exemplary embodiments the order of placement of variable optic and depositing of monomer mixture may be reversed. At step 714, the first mold part is placed proximate to a second mold part to form a lens-forming cavity with at least some of the reactive monomer mixture and the variable optic insert in the cavity. As discussed above, preferred embodiments include an energy source and one or more components also within the cavity and in electrical communication with the variable optic insert.

At step 715, the reactive monomer mixture within the cavity is polymerized. Polymerization may be accomplished, for example, via exposure to one or both of actinic radiation and heat. At step 716, the ophthalmic lens is removed from the mold parts with the variable optic insert adhered to or encapsulated within the insert-encapsulating polymerized material making up the ophthalmic lens.

Although the method of the present invention herein may be used to provide hard or soft contact lenses made of any known lens material, or material suitable for manufacturing such lenses, preferably, the lenses of the present invention are soft contact lenses having water contents of up to about 90 percent. More preferably, the lenses are made of monomers containing hydroxy groups, carboxyl groups, or both or be made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, silicone hydrogels made from silicone macromers and hydrophilic monomers.

Apparatus

Figure 8:
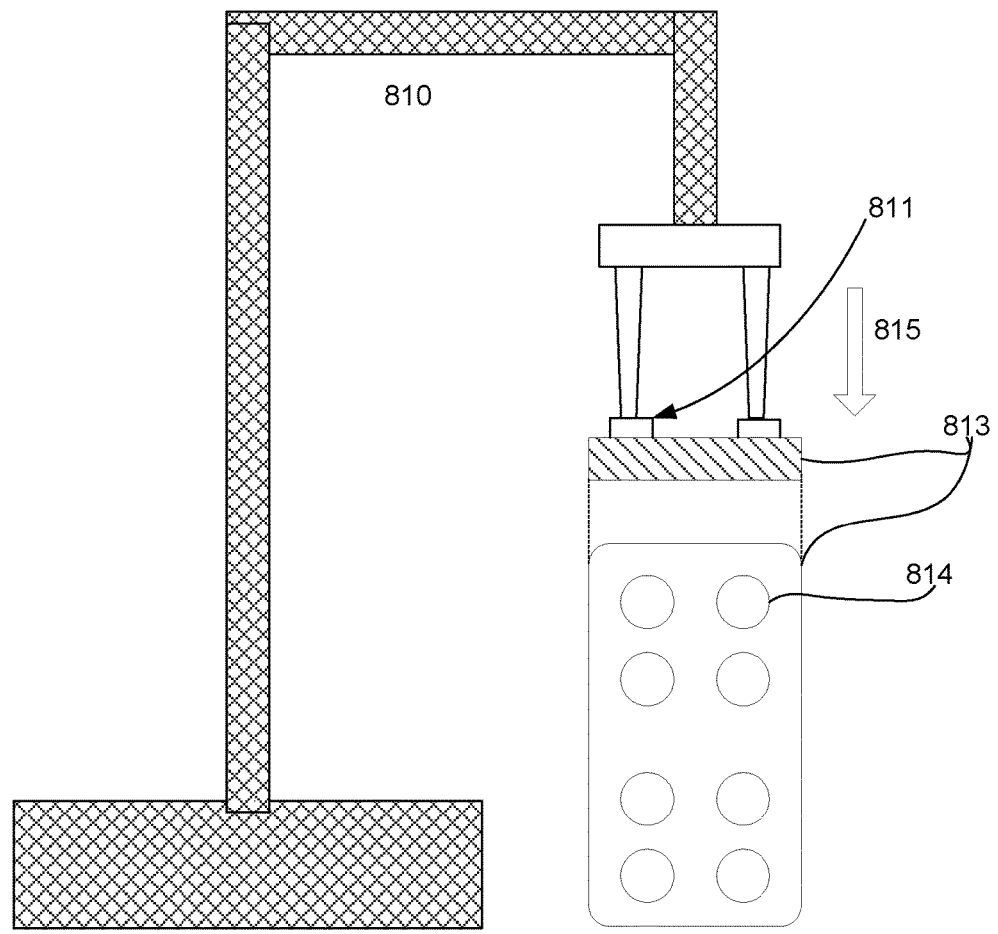
FIG. 8 illustrates an example of apparatus components for placing a variable optic insert comprised of liquid crystal into an ophthalmic lens mold part.

Referring now to FIG. 8, automated apparatus 810 is illustrated with one or more transfer interfaces 811. Multiple mold parts, each with an associated variable optic insert 814 are contained on a pallet 813 and presented to transfer interfaces 811. Exemplary embodiments may include, for example, a single interface individually placing variable optic insert 814, or multiple interfaces (not shown) simultaneously placing variable optic inserts 814 into the multiple mold parts, and in some embodiments, in each mold part. Placement may occur via vertical movement 815 of the transfer interfaces 811.

Another aspect of some exemplary embodiments of the present invention includes apparatus to support the variable optic insert 814 while the body of the ophthalmic lens is molded around these components. In some exemplary embodiments the variable optic insert 814 and an energy source may affixed to holding points in a lens mold (not illustrated). The holding points may be affixed with polymerized material of the same type that will be formed into the lens body. Other exemplary embodiments include a layer of prepolymer within the mold part onto which the variable optic insert 814 and an energy source may be affixed.

Processors Included in Insert Devices

Figure 9:
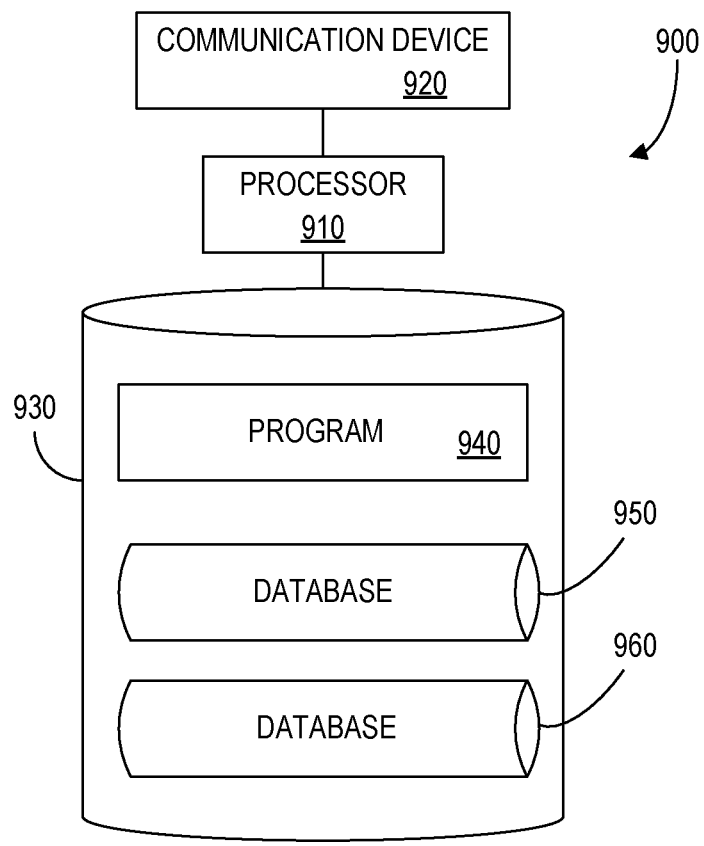
FIG. 9 illustrates a processor that may be used to implement some embodiments of the present invention.

Referring now to FIG. 9, a controller 900 is illustrated that may be used in some exemplary embodiments of the present invention. The controller 900 includes a processor 910, which may include one or more processor components coupled to a communication device 920. In some exemplary embodiments, the controller 900 may be used to transmit energy to the energy source placed in the ophthalmic lens.

The controller may include one or more processors, coupled to a communication device configured to communicate energy via a communication channel. The communication device may be used to electronically control one or more of the placement of a variable optic insert into the ophthalmic lens or the transfer of a command to operate a variable optic device.

The communication device 920 may also be used to communicate, for example, with one or more controller apparatus or manufacturing equipment components.

The processor 910 is also in communication with a storage device 930. The storage device 930 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 930 may store a program 940 for controlling the processor 910. The processor 910 performs instructions of the program 940, and thereby operates in accordance with the present invention. For example, the processor 910 may receive information descriptive of variable optic insert placement, processing device placement, and the like. The storage device 930 may also store ophthalmic related data in one or more databases 950, 960. The database 950 and 960 may include specific control logic for controlling energy to and from a variable optic lens.

In this description, reference has been made to elements illustrated in the figures. Many of the elements are depicted for reference to depict the embodiments of the inventive art for understanding. The relative scale of actual features may be significantly different from that as depicted, and variation from the depicted relative scales should be assumed within the spirit of the art herein. For example, liquid crystal molecules may be of a scale to be impossibly small to depict against the scale of insert pieces. The depiction of features that represent liquid crystal molecules at a similar scale to insert pieces to allow for representation of factors such as the alignment of the molecules is therefore such an example of a depicted scale that in actual embodiments may assume much different relative scale.

Figure 10A:
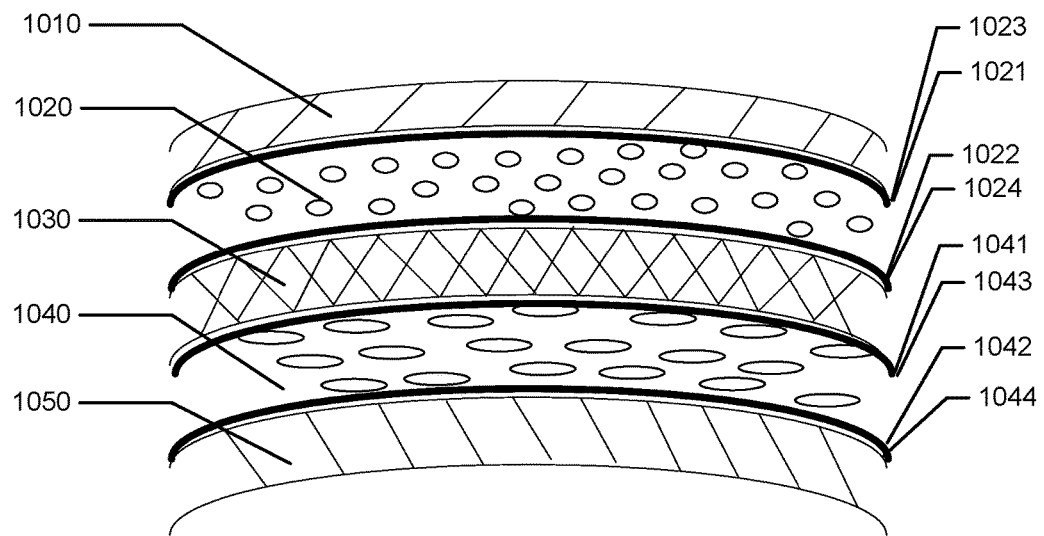
FIG. 10A illustrates layers involved in an exemplary electroactive liquid crystal two chamber based focal accommodating lens.

Referring to FIG. 10A an exemplary two chamber liquid crystal electroactive lens is illustrated in cross section so that one may perceive the various layers involved. A first plastic lens piece, the front optic piece 1010 may define the topmost front curve piece of a lens insert. There may be numerous layers with different functions upon the lens insert pieces. In the illustrated example there may be an electrode layer 1021 which is transparent and which in some examples may be formed of a layer of ITO or a deposited layer of graphene, graphene oxide or carbon nano-tubules for example. Upon the electrode layer 1021 may be an alignment layer 1023 as have been describe earlier. There may be self-aligned layers of material such as Silicon oxide (SiOx) or in other examples photoactive chemically bound alignment molecular layers. In proximity to the alignment layer 1023 may be a first liquid crystal layer 1020, which in some examples may be a layer of polymer liquid crystal or liquid crystal polymer liquid crystal. The polymerized liquid crystal layer 1020 is illustrated in a linearly aligned layer where the direction of the liquid crystals is oriented in and out of the paper. The liquid crystal layer may be sandwiched on the other side with an alignment layer 1024 and an electrode layer 1022. The electrode layer 1022 and alignment layer 1024 may be located upon an intermediate optic piece 1030. The intermediate optic piece 1030 may allow for the defining of a two chamber lens element. On the other side of the intermediate optic piece 1030 may be layers that define the top curve of the second liquid crystal chamber. There may be an alignment layer 1043 and an electrode layer 1041. In the second chamber may be a second liquid crystal layer 1040. This second liquid crystal layer 1040 may also be a polymerized layer where the direction of the liquid crystal molecules may be aligned in the page from left to right as illustrated which is essentially perpendicular to the alignment in the first chamber. The bottom of the second chamber may have the bottom optic piece 1050 with deposited layers of a second chamber bottom electrode layer 1042 and a second chamber bottom alignment layer 1044. The combination of three plastic pieces and two aligned liquid crystal layers with alignment layers and electrodes may complete a lens element in some examples.

Figure 10B:
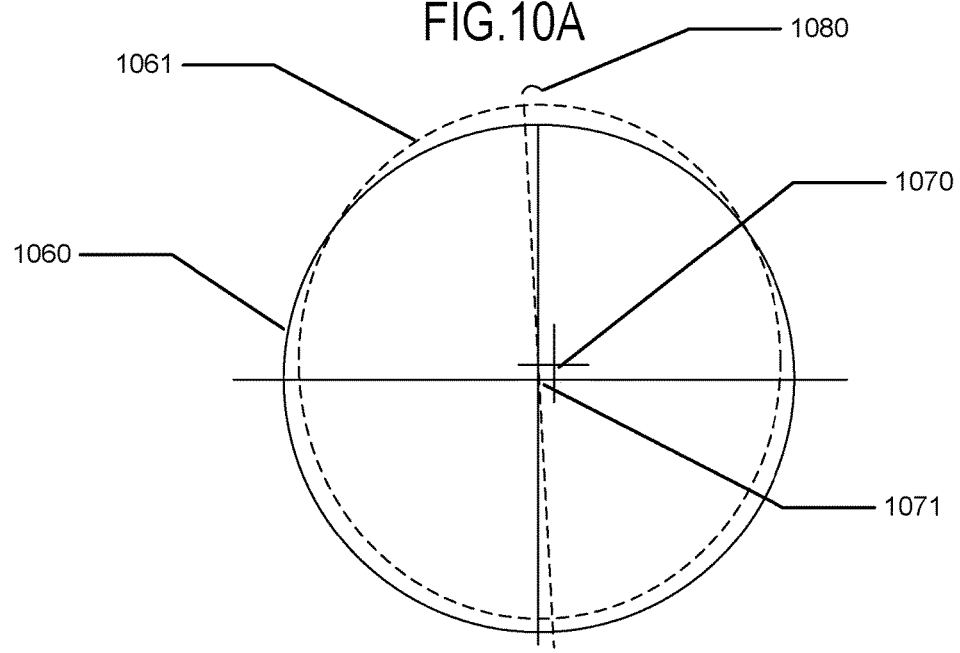
FIG. 10B illustrates aspects of non-optimal conditions that may occur in the fabrication of the exemplary two chamber based focal accommodating lens.

Referring to FIG. 10B an illustration of various types of non-optimal aspects of the fabrication of the lens element of FIG. 10A is shown. In a first type of non-optimal aspect, either one or both of the chambers may be formed where the optical center of the lens element may not be at the physical center of the lens components. In the illustration of FIG. 10B, the optical center 1071 of one lens may be offset from the optical center 1070 of the other lens element. In some examples, the front optic piece 1061 may be offset from the bottom optic piece 1060. This offset may be the cause of non-optimal lens center alignment. In another example, there may be an offset 1080 of the axis of rotation between the alignment of the first chamber and the second chamber. Ideally in some examples, the two chambers may be oriented ninety degrees from each other, but depending on the processing there may be a rotation offset around the center of the lens that causes the offset 1080 between the ideal 90 degree orientation and the actual orientation. There may be methods of processing the lens layers that allow for minimization of these errors. In some examples, oriented liquid crystal layers may be inspected with equipment that measures the optical center of the lens and allows for movement of lens pieces before they are fixed in place. In other examples, the alignment layers for the liquid crystals may be oriented using photosensitive alignment layers where the alignment may be influenced or defined by irradiation of the alignment layer.

Figure 10C:
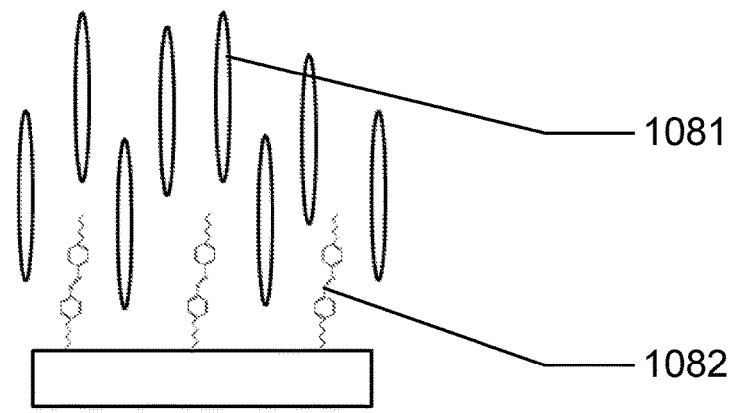
FIGS. 10C-10E illustrate exemplary depictions of the influence of alignment layers upon liquid crystal molecules and the formation of patterns in exemplary manners.

Referring to FIG. 10C, a close up depiction of an example of alignment layer molecules in an orienting layer 1082 interacting with liquid crystal molecules 1081 may be found. In a non limiting example, the alignment layer molecule may be an Azobenzene moiety. The orientation of phenyl groups in the azobenzene moiety may occur in a relatively linear fashion as depicted at 1082. In some examples, one stabile configuration of the azobenzene moiety may place the aromatic ring portions of the moiety in a trans-configuration where the rings are located on opposite sides of an intervening double bonded chemical bond. This may be the configuration depicted at 1082 and may result in a long liner shape to the molecule. As depicted the interaction of the exemplary azobenzene moiety with liquid crystal molecules may cause them to align along the axes of the azobenzene moieties.

Figure 10D:
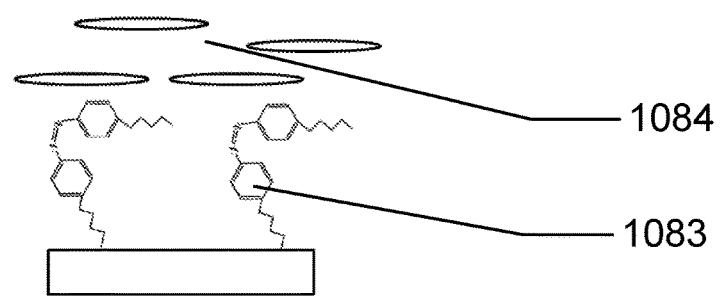

Referring to FIG. 10D, a close up depiction of an example of an alternative orientation of molecules in the orienting layer is depicted at 1083 interacting with liquid crystal molecules 1084. For exemplary azobenzene moieties the depiction at 1083 may represent a second configuration of the azobenzene moiety backbone where the aromatic ring portions of the ring are oriented in a cis-configuration. As depicted this may place the end portions of the molecule into a configuration that is more parallel to the optic piece surface. The liquid crystal molecules, at 1080 may in an exemplary manner now align with the parallel orientation of the alignment molecules. In some examples the orientation at 1082 and at 1083 may impart the maxima and minima of the effective index of refraction into the liquid crystal layers.

Figure 10E:
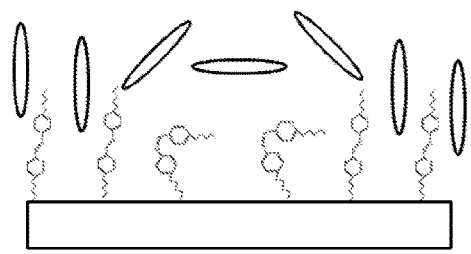

Referring now to FIG. 10E, a close up depiction of a combination of different alignment layer configurations is depicted in an exemplary fashion. In regions where the orientation is dominated by parallel configurations relative to the insert piece surface the liquid crystal molecules may be primarily oriented parallel to the surface. Alternatively in the regions dominated by perpendicular molecules the liquid crystal molecules may thereabout be aligned primarily in an orientation perpendicular to the surface. In between these extreme orientations the molecules may be aligned based on the average configuration of alignment molecules. As shown in the figure this may result in an effective intermediate orientation. In this manner a distribution of orientations of the liquid crystal molecules may be controlled in such a manner to allow for the creation of gradient indexed patterns of liquid crystal molecules where the effective index of refraction is smoothly varied from one extrema to another across the dimensions of the lens elements. *Fred. We should put in some numbers here and in the drawings.

Figure 11A:
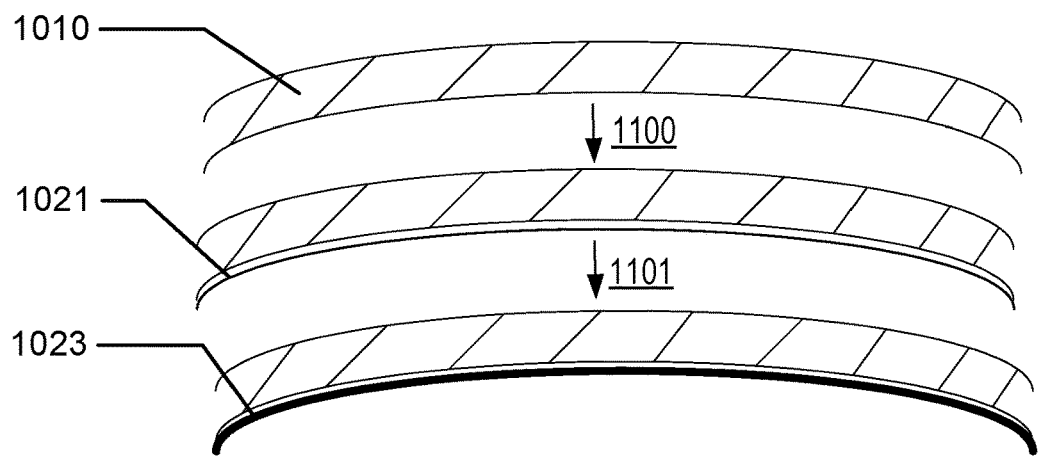

Referring now to FIG. 11A processing steps for the various exemplary layers may be depicted. The front optic piece 1010 may be processed at step 1100 to deposit an electrode layer 1021 upon the surface. In some examples the layer may be deposited ITO. The processed front optic piece may be held while the other optic pieces are processed. An alignment layer 1023 may be placed upon the electrode layer 1021. In some examples, the processing of the optic piece may occur in parallel or in any order possible.

Figure 11B:
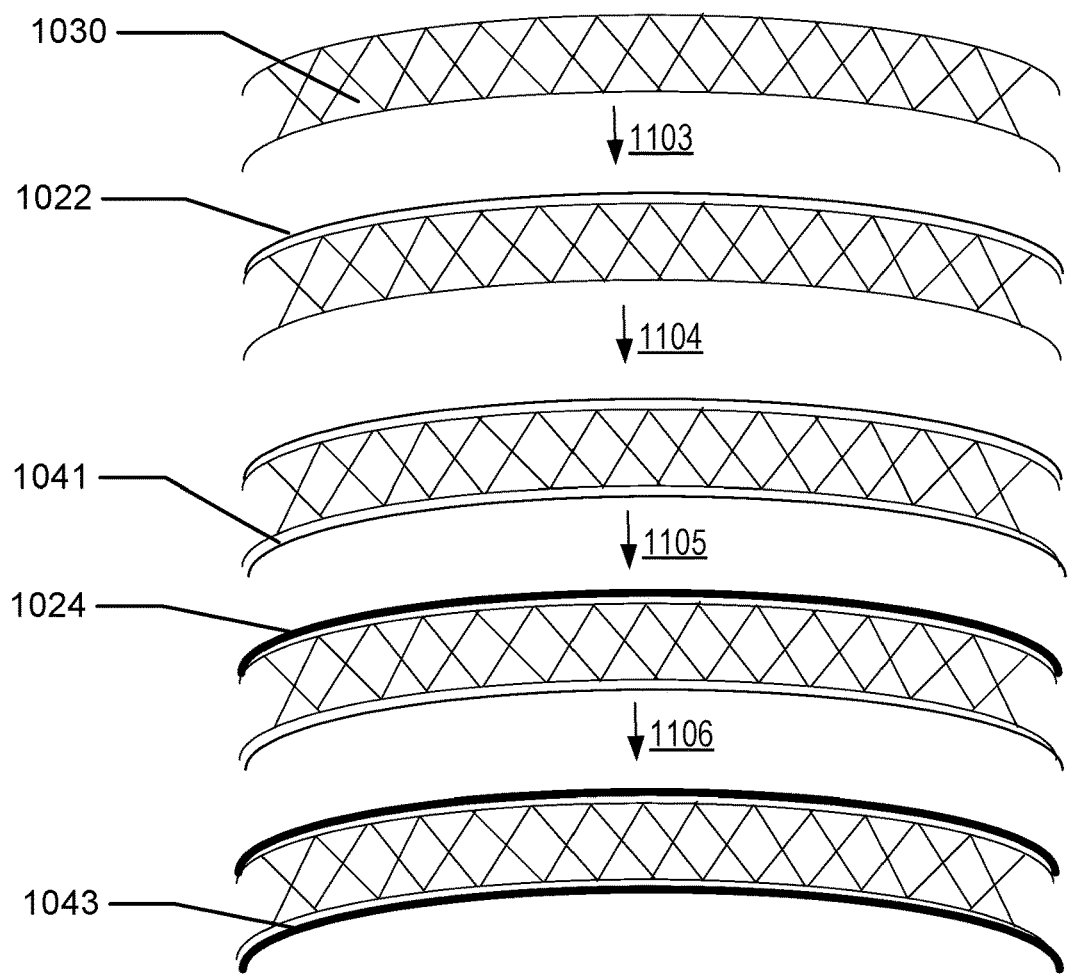

Referring to FIG. 11B processing steps for the various exemplary layers may be depicted in reference to the intermediate optic piece 1030. Since there are two surfaces of the middle optic piece that may have processing upon them, the processing of the intermediate optic piece may be more complicated. In some examples, at step 1103 the top surface of the intermediate optic piece may have a transparent, electrode layer 1022 deposited upon it. At step 1104 the bottom surface of the intermediate optic piece may have a second chamber top electrode layer 1041 deposited upon it. In some examples the processing of steps 1103 and 1104 may occur simultaneously. Next at step 1105 an alignment layer 1024 may be formed upon the top surface of the intermediate optic piece. The alignment layer 1024 may be a photosensitive alignment layer. Next at step 1106 the bottom surface of the intermediate optic piece may have an alignment layer 1043 deposited upon it, where again, the alignment layer 1043 may be photosensitive.

Referring now to FIG. 11C processing steps for the various exemplary layers may be depicted. The bottom optic piece 1050 may be processed at step 1107 to deposit an electrode 1042 upon the surface. In some examples the layer may be deposited ITO. In another example a layer of graphene oxide may be deposited upon the bottom optic piece 1050. Next at step 1108, a layer of photosensitive alignment molecules, such as azobenzene based alignment material, may be deposited upon the electrode layer to form an alignment layer 1044. In some examples, there may be other layers that are deposited between the electrode and the alignment layer. The processed front optic piece may be held while the other optic pieces are processed. In some examples, the processing of the optic pieces may occur in parallel or in any order possible.

Referring now to FIG. 11D, the three pieces, front optic piece 1010, intermediate optic piece 1030, and bottom optic piece 1050, all with their deposited layers upon them, may be assembled into a single stack of pieces in step 1109. This pieces may still be able to be moved in relationship to each other, however, they form both a first cavity 1110 and a second cavity 1111.

Figure 11E:
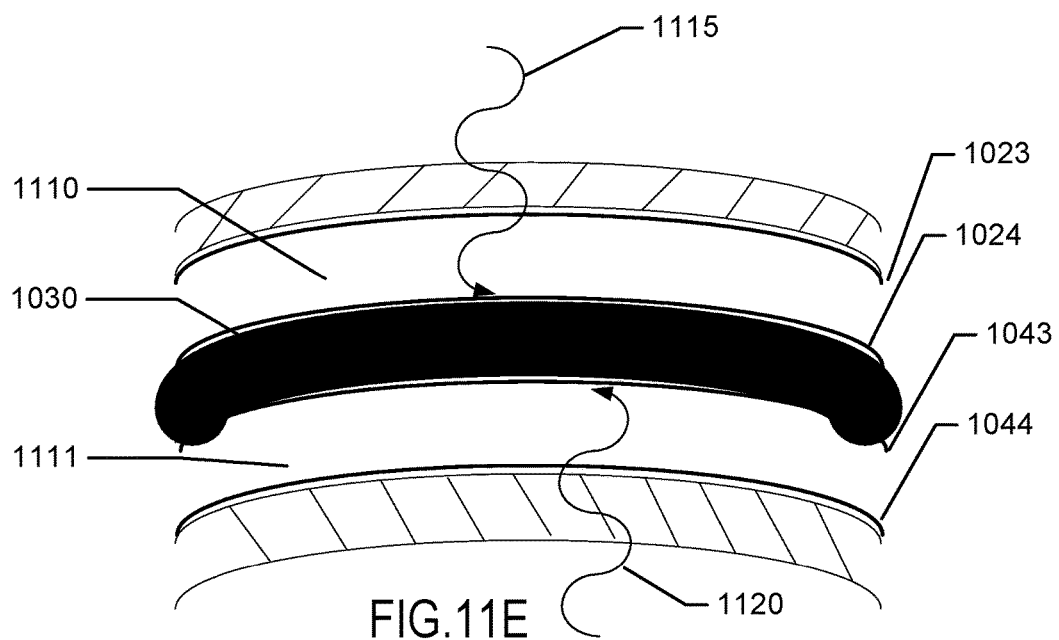

In some examples, the alignment layers may have been formed by deposition processes so that they are already defined on the pieces with an alignment locked in. In these cases it may be important to rotate the top and/or bottom pieces to ensure that the alignment layers of the top and bottom chambers is an intended ninety degrees relative from each other. In another example, as mentioned the alignment layers may be photoactive. Referring to FIG. 11E, an example of forming the orientation of alignment layers is illustrated. In the figure, the intermediate optic piece 1030 is illustrated in complete dark shading. This illustrates the fact that the intermediate lens plastic may be formed with an amount of a UV dye incorporated. The UV dye may essentially absorb all the UV light typically used with photosensitive alignment layer processes. In some examples the UV dye or blocker may be a benzotriazole-type UV blocker such as NORBLOC 7966. Other formulations for the UV blocker may include 2-(4-Benzoyl-3-hydroxyphenoxy)ethyl acrylate which may be called UV 416, 4-Methacryloxy-2-hydroxybenzophenone which may be called UV 725 or Pharnorcia 725, 2-(2'-Hydroxy-5'-methacryloxyethylphenyl)-2H-benzotriazole which as mentioned previously may be called Norbloc 7966, 2-Phenylethyl methacrylate which may be called UV 123, 2-Phenylethyl acrylate which may be called UV 367, 4-[(E)-phenyldiazenyl]phenyl-2-methacrylate which may be called BL01, or 2-(2'-Hydroxy-3'-Methallyl-5'-MethylPhenyl)-benzotriazole which may be called BL02 amongst other examples of UV absorbing molecules that may be used in contact lenses. This allows for the aspect of the following procedures to create an alignment axis in the first chamber that is accurately perpendicular to the alignment axis of the second chamber to a machine level of accuracy. A machine may be used to irradiate polarized light that is precisely perpendicular to each other from both the bottom and the top of the lens stack. Then a top polarized light source 1115 may be oriented perpendicularly to a bottom polarized light source 1120. The photosensitive alignment layers in the top chamber or first cavity 1110 including alignment layer 1023 and alignment layer 1024 may be influenced to align with the top polarized light source 1115. In contrast, the alignment layers 1043 and 1044 in the second cavity 1111 may be aligned with the bottom polarized light source 1120. Since the intermediate optic piece 1030 may be opaque to the wavelengths of the polarized light sources the patterns of the two sources may not interfere with each other. Furthermore, in some examples, the absorbance spectrum of the UV dyes may be narrow such that there is no observable effect of the dye in the visible spectrum. In such cases, the UV absorbance may provide additional benefits to a user while also accomplishing the desired processing effects.

In some examples, the nature of the alignment layers may be more complex. For example, the alignment layers on the intermediate optic piece may be deposited layers while the other alignment layers may be photosensitive. For example, the deposited layers may be formed such that they favor homeotropic alignment of the liquid crystal. In this case, the outermost alignment layers may be the photosensitive layers. The same type of processing as laid out previously may be performed. In some other examples, the chambers may be filled with liquid crystal layers which may contain UV sensitive dyes. The combination of linear alignment and homeotropic alignment on the other side of the layer may still form a layer with linear alignment aspects.

Figure 11F:
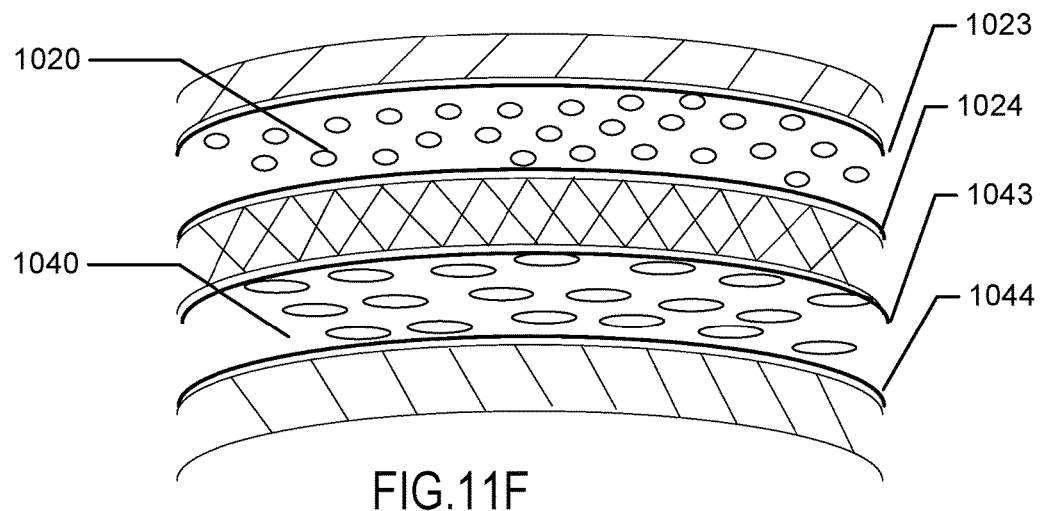

Referring to FIG. 11F, in some examples a layer of liquid crystal material may now be filled into the first cavity creating a first liquid crystal layer 1020 and the second cavity creating a second liquid crystal layer 1040. In some examples, the liquid crystal layers may be layers of liquid crystal polymer with liquid crystal mixed into a solution of polymerizerable monomer. In other examples a polymer material having chemically bonded liquid crystal molecules may have liquid crystal mixed in while it is a monomer liquid. Since the chambers have alignment layers 1023, 1024, 1043 and 1044 established, the liquid crystal molecules will assume an orientation that is directed by the alignment layers' orientation. After an appropriate time for the liquid crystal layers to relax into the aligned configuration, the layers may be aligned and the effect of their alignment may allow for their optical properties in the aligned states to be measured.

Figure 11G:
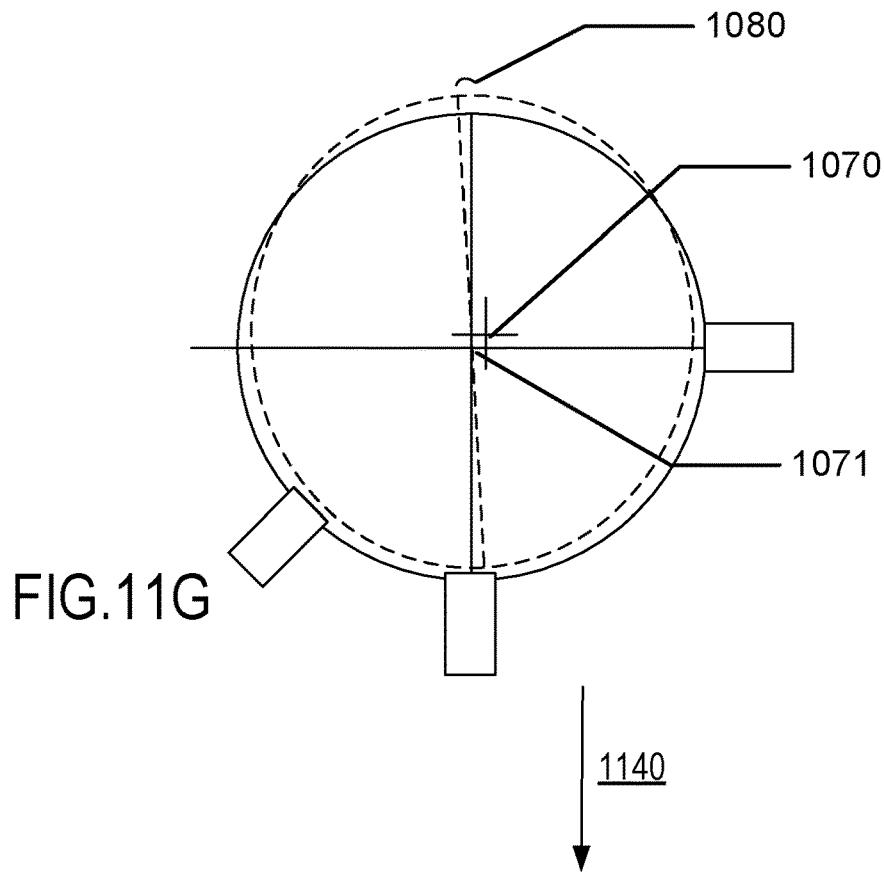
Figure 11H:
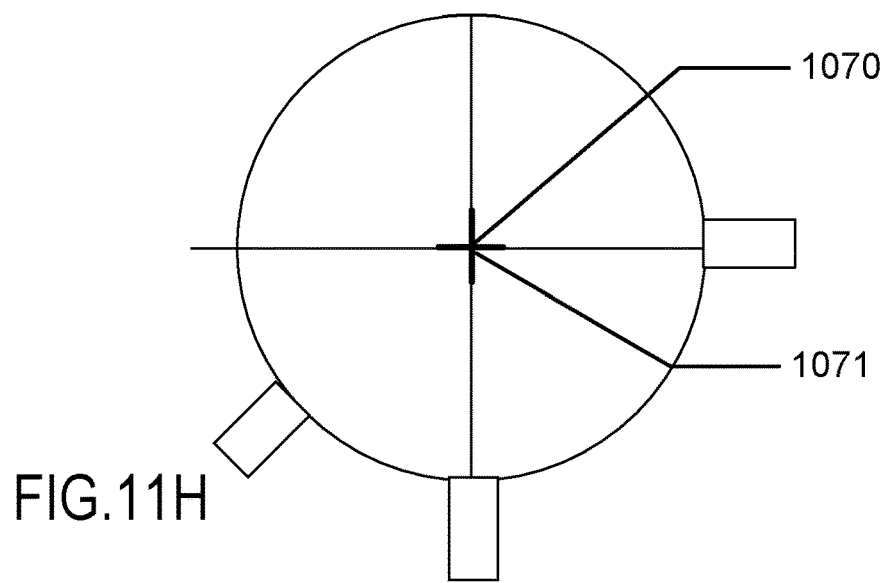

Referring to FIG. 11G, a measurement process may be depicted of the aligned liquid crystal layers. As previously discussed in reference to FIG. 10B there may be numerous non-optimal conditions that may be measured, such as a mismatch of centration illustrated by the difference between optical center 1070 and optical center 1071. There may be rotational mismatch as illustrated by the angle of offset 1080. At step 1140, the individual optic pieces may be manipulated to translate them in an x and y direction or rotate them around a particular axis or to undergo both movements. Since the layers are stacked but not sealed or affixed to each other these translations may be performed to fix the non-desired conditions and result in a more optimal lens combination as depicted in reference to FIG. 11H where the two measured optical centers 1071 and 1070 may both lie on top of each other and in the desired center of the lens stack. In some cases, where the optical axis of the two chambers is not set with machine accuracy by photoalignment means, the optical axes may also be measured and rotation of one or more pieces may bring them into perpendicular alignment.

Referring now to FIG. 11I, after the various measurements have been performed and adjustments have been made to the lens optic pieces, then the lens insert can be locked into its orientation. In some examples, this may occur by sealing or gluing the edge of the optic pieces together. In some other examples, a melting apparatus such as a laser may melt and fuse the edges of the optic pieces together. In the FIG. 11I another example is illustrated where a polymer material is included with the liquid crystal layers, including first liquid crystal layer 1020 and second liquid crystal layer 1040 in the chambers. In some examples an exposure to light, typically in the UV spectrum may catalyze polymerization of the liquid crystal layer and the monomer mixed with it. The resulting polymerization may lock the liquid crystal molecules into their aligned orientation. In some examples the monomers may also be bound to liquid crystal molecules which may also influence polymerization to occur in such a way that the bound liquid crystal molecules may align with the alignment layers as well as the unbound liquid crystal molecules. In examples where the intermediate optic absorbs ultraviolet radiation, it may be necessary to provide radiation from both sides of the stack such as irradiation 1160 from the front of the stack and irradiation 1161 from the back of the stack. In other examples, the polymerization may be catalyzed in other manners such as by heating of the stack. Once the layers in the chambers have been polymerized the chambers may be sealed by the polymerization process itself. In other examples, the edges may be sealed or glued to provide additional sealing of the liquid crystal layers. In some examples, the stacked pieces were held in place by clamps before either the polymerization or the sealing processes, and after sealing the stack pieces may now be released.

Referring to FIG. 12 a method for forming a liquid crystal electroactive lens element is illustrated. At step 1201, the front, intermediate and back optic pieces of a two chamber or more insert piece are formed. In some examples, the intermediate optic piece may be formed with a UV dye interspersed in the form. At step 1202 an electrode layer may be deposited upon the lower surface of the front optic piece, both surfaces of the intermediate optic piece and the upper surface of the back optic piece. In some examples one or more of the electrodes may be omitted. At step 1203, a photosensitive alignment layer may be deposited upon the electrode layers on the front, intermediate and back optic pieces. In some examples, there may be intervening layers such as insulator films between the electrode layer and the photosensitive alignment layer. At step 1204, the front optic piece may be positioned above the intermediate optic piece. The intermediate optic piece may be positioned above the back optic piece forming a stack with cavities or chambers that may be aligned with each other. There may be a top or first cavity and a bottom or second cavity. At step 1205, the front of the stack may be irradiated with a first pattern of light. In some examples, the light pattern may be polarized along a first linear polarization axis. The stack may be irradiated from the back with a second pattern of light which may be a second linear polarization pattern along an axis perpendicular to the first linear polarization axis. The wavelength of the irradiations may be at a wavelength or a band of wavelengths that interact with the photo sensitive alignment layer. At step 1206, a liquid crystal containing liquid may be deposited into the first cavity and a liquid crystal containing liquid may be deposited into the second cavity. In some examples the liquid crystal may be intermixed into a polymerizerable monomer liquid that may be a monomer with portions comprising a bound liquid crystal. The liquid crystal portions may be allowed to interact with the alignment layers and thereby become aligned during step 1207. Next, at steps 1208 and 1209 a measurement may be performed on the optical devices. The first optical chamber may be measured with light of a first polarization where the polarization is made to align with the liquid crystal molecules in the first chamber in step 1208. In a second step the measurement may be repeated with a perpendicular polarization which selectively probes molecules in the second chamber in step 1209. The measurements of each chamber may be compared to a theoretical measurement for the designed chamber of liquid crystal. Also, the results for the two chambers may be compared to each other to evaluate the degree to which the orientations are appropriately perpendicular or orthogonal to each other. At step 1210, evaluation of the measurement result may allow for determination of any adjustments that may be needed for optimal results such as the translation of one or more of the optic pieces in one or more directions or rotation of the pieces relative to each other. Once the adjustments have been made, in some examples the measurement process may be repeated. Next at step 1211, the monomer containing liquid crystal may be exposed to a condition that may cause the monomer to polymerize such as exposure to irradiation or to heat. Next at step 1212, there may be an optional sealing of the plastic parts to each other. In some cases the polymerized monomer in the chambers may be a sealing means in itself otherwise a seal material such as an adhesive or a welding process by laser melting for example may be performed on the edges of the optic pieces. The results of the method may be a well aligned set of lens elements with an electroactive layer containing liquid crystal material with optimized optical performance.

Figure 13A:
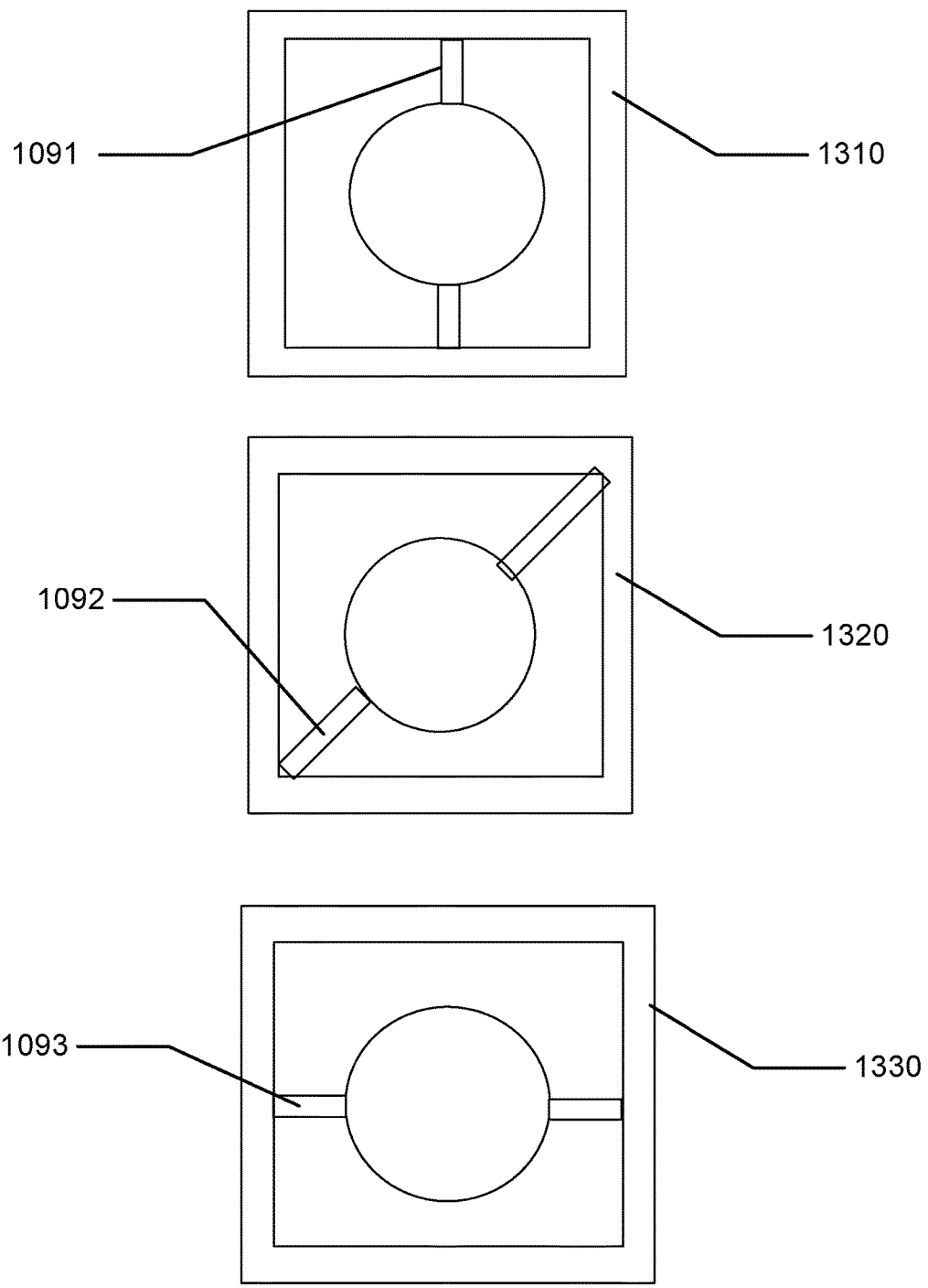

Referring to FIG. 13A, an example of a support frame that may hold the optic pieces so that they may be assembled and adjusted is illustrated. The illustrations shows a single optic piece in a frame, but in some examples, there may be multiple optic pieces that may be processed in parallel. A front optic piece in a frame 1310 may include an alignment tab 1091. An intermediate optic piece in a frame 1320 may include an alignment tab 1092. A back optic piece in a frame 1330 may include an alignment tab 1093. The alignment frames may be moved by an external piece of equipment to adjust them.

Referring to FIG. 13B, the three optic pieces in frames may be assembled together into a stack as illustrated. While the pieces are put together, the liquid crystal layers may be added into the stack. The assembled pieces and liquid crystal layers may form an active optic piece. For example, at FIG. 13C, incident light may be polarized along the direction of the aligned liquid crystal molecules of one of the chambers. A wavefront interferometer may characterize the optic characteristics of the lens. In FIG. 13C, an exemplary superimposed optical wavefront is illustrated. The example may indicate that a combination of "X" and "Y" axis movements of the front optic piece may be needed. In FIG. 13D, an exemplary superimposed optical wavefront is illustrated. This illustration may show a good alignment of the lens cavity which is aligned along the other axis of polarization. After adjustment of the frames appropriate for the measured wavefronts, the lens may be ready to be locked into position by either or both of polymerization of the liquid crystal containing liquid layer or sealing of the edge of the optic pieces.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method of forming a variable optic insert for an ophthalmic lens device comprising:
    forming a front optic piece;
    forming an intermediate optic piece, wherein the intermediate optic piece comprises a UV absorbing dye, wherein the UV absorbing dye absorbs sufficient radiation to isolate processing of UV sensitive layers located above and beneath the intermediate optic piece;
    forming a back optic piece;
    adding a photosensitive alignment layer to surfaces of the front optic piece, the intermediate optic piece, and the back optic piece, wherein the photosensitive alignment layer is not the same chemical as the UV absorbing dye;
    placing the intermediate optic piece upon the back optic piece;
    placing the front optic piece upon the intermediate optic piece, wherein a combination of the front optic piece, the intermediate optic piece and the back optic piece form a stack;
    exposing the photosensitive alignment layers underneath the intermediate optic piece with a first polarized irradiation source in a first polarization pattern, wherein a wavelength of the irradiation is essentially completely absorbed by the UV absorbing dye; and
    exposing the photosensitive alignment layers above the intermediate optic piece with a second polarized irradiation source in a second polarization pattern, wherein a wavelength of the irradiation is essentially completely absorbed by the UV absorbing dye.

2. The method according to claim 1 further comprising:
    filling a first cavity between the front optic piece and the intermediate optic piece with a solution comprising liquid crystal molecules forming a first liquid crystal layer;
    filling a second cavity between the intermediate optic piece with the solution comprising liquid crystal molecules forming a second liquid crystal layer; and
    allowing the solution in the filled cavities to adjust to align with the patterns of the photosensitive alignment layers.

3. The method according to claim 2 further comprising:
    measuring focal characteristics of the first liquid crystal layer between the front optic and the intermediate optic, wherein the measuring involves using polarized light aligned in the polarization pattern of the second polarization pattern.

4. The method according to claim 3 further comprising:
    measuring focal characteristics of the first liquid crystal layer between the front optic and the intermediate optic, wherein the measuring involves using polarized light aligned in the polarization pattern of the second polarization pattern, wherein an electrical potential is applied across a first electrode and a second electrode surrounding the first liquid crystal layer between the front optic and the intermediate optic.

5. The method according to claim 4 further comprising:
    measuring polarization characteristics of the liquid crystal layer between the intermediate optic and the back optic, wherein the electrical potential applied across the first electrode and the second electrode surrounding the first liquid crystal layer between the front optic and the intermediate optic temporarily removes at least some polarization patterning of the first liquid crystal layer between the front optic and the intermediate optic.

6. The method according to claim 4 further comprising:
    calculating a focal center of an optical device formed by the first liquid crystal layer between the front optic and the intermediate optic.

7. The method according to claim 6 further comprising:
    adjusting a position of one or more of the front optic the intermediate optic piece and the back optic piece by translation along one or both perpendicular axes in a plane of the variable optic insert.

8. The method according to claim 7 wherein the adjusting the position is performed based on the calculating of the focal center.

9. The method according to claim 8 further comprising:
polymerizing the solution comprising liquid crystal molecules in the first cavity; and
polymerizing the solution comprising liquid crystal molecules in the second cavity.

10. The method according to claim 5 further comprising:
adjusting a position of one or more of the front optic the intermediate optic piece and the back optic piece by rotation around a physical center of the variable optic insert.

11. The method according to claim 10 further comprising:
polymerizing the solution comprising liquid crystal molecules in the first cavity; and
polymerizing the solution comprising liquid crystal molecules in the second cavity.

12. The method according to claim 1 wherein the UV absorbing dye comprises a benzotriazole-type UV blocker.

13. A method of forming a variable optic insert for an ophthalmic lens device comprising:
forming a front optic piece;
forming an intermediate optic piece, wherein the intermediate optic piece comprises a UV absorbing dye wherein the UV absorbing dye absorbs sufficient radiation to isolate processing of UV sensitive layers located above and beneath the intermediate optic piece;
forming a back optic piece;
adding a photosensitive alignment layer to surfaces of the front optic piece, the intermediate optic piece, and the back optic piece;
placing the intermediate optic piece upon the back optic piece;
placing the front optic piece upon the intermediate optic piece, wherein a combination of the front optic piece, the intermediate optic piece and the back optic piece form a stack;
exposing the photosensitive alignment layers underneath the intermediate optic piece with a first polarization pattern;
exposing the photosensitive alignment layers above the intermediate optic piece with a second polarization pattern;
filling a first chamber between the front optic piece with a liquid crystal containing monomer mixture;
filing a second chamber between the intermediate optic piece and the back optic piece with a liquid crystal containing monomer mixture;
measuring optical characteristics of the stack with a first polarized incident light source;
measuring optical characteristics of the stack with a second polarized incident light source:
adjusting an orientation of one or both of the front optic piece and the back optic piece;
polymerizing the liquid crystal containing monomer mixture in the first chamber; and
polymerizing the liquid crystal containing monomer mixture in the second chamber.

14. A method for forming a multi-cavity insert for an ophthalmic device, the method comprising:
forming a front optic piece;
forming a back optic piece;
forming an intermediate optic piece, wherein a composition of the intermediate optic piece blocks more than 90% of UV light in a first band of UV light, wherein the composition which blocks more than 90% of UV light prevents light is used in forming the ophthalmic device and blocks UV light from passing through the intermediate piece allowing irradiating of both sides of the intermediate piece in different ways simultaneously;
stacking the front optic piece upon the intermediate optic piece upon the back optic piece, wherein a first cavity is formed between the front optic piece and the intermediate optic piece and a second cavity is formed between the intermediate optic piece and the back optic piece;
irradiating an extent of the first cavity with a source of UV light from a first direction which traverses the front optic piece, wherein the source of UV light emits light within the first band of UV light, and wherein the irradiation is incident upon materials within the first cavity; and
irradiating an extent of the second cavity, simultaneously with the irradiating of the extent of the first cavity, with a source of UV light from a second direction which traverses the back optic piece, wherein the source of UV light emits light within the first band of UV light, and wherein the irradiation is incident upon materials within the second cavity.

* * * * *